US005756083A

United States Patent [19]
Elliott

[11] Patent Number: 5,756,083
[45] Date of Patent: May 26, 1998

[54] MPL LIGAND ANALOGS

[75] Inventor: Steven G. Elliott, Newbury Park, Calif.

[73] Assignee: Amgen Inc., Thousand Oaks, Calif.

[21] Appl. No.: 591,070

[22] Filed: Feb. 9, 1996

Related U.S. Application Data

[63] Continuation-in-part of Ser. No. 388,779, Feb. 15, 1995, Pat. No. 5,696,250.

[51] Int. Cl.$^6$ .................. A61K 38/19; C07K 14/52
[52] U.S. Cl. .................. 424/85.1; 530/351; 435/69.5; 435/325; 435/358; 435/360; 435/252.3; 435/320.1
[58] Field of Search .................. 530/351; 435/69.5, 435/325, 358, 252.3, 320.1, 360; 424/85.1

[56] References Cited

U.S. PATENT DOCUMENTS

| | | | |
|---|---|---|---|
| 5,217,881 | 6/1993 | Park | 435/69.5 |
| 5,218,092 | 6/1993 | Sasaki et al. | 530/351 |

FOREIGN PATENT DOCUMENTS

| | | |
|---|---|---|
| 0 428 267 A2 | 10/1990 | European Pat. Off. . |
| 0 668 352 A1 | 8/1995 | European Pat. Off. . |
| 0 675 201 A1 | 10/1995 | European Pat. Off. . |
| 2 714 670 A1 | 7/1995 | France . |
| 195 00 030 A1 | 7/1995 | Germany . |
| WO 95/05465 | 2/1995 | WIPO . |
| WO 95/18858 | 7/1995 | WIPO . |
| WO 95/21919 | 8/1995 | WIPO . |
| WO 95/21920 | 8/1995 | WIPO . |
| WO 95/26746 | 10/1995 | WIPO . |
| WO 96/17062 | 6/1996 | WIPO . |
| WO 96/23888 | 8/1996 | WIPO . |

OTHER PUBLICATIONS

Eaton et al., "Biological Activity of Human Thrombopoietin (TPO), the C-mpl Ligand and TPO Variants and the Chromosomal Localization of TPO", Blood, 84(10), (1994); Abstract No. 948, XP 000567760.

Hoffman, et al., "Peptide, disulfide, and glycosylation mapping of recombinant human thrombopoietin from Ser1 to Arg246", Biochemstry, 35(47), pp. 14849–14861, (1996).

Delorme et al. (1992) Biochemistry 31:9871–9876.

Bose et al. (1976). J. of Biol. Chem. vol. 251, No. 6, pp. 1659–1662.

Lok et al. (1994) Nature vol. 369 pp. 565–568.

Primary Examiner—John Ulm
Assistant Examiner—Prema Mertz
Attorney, Agent, or Firm—Robert R. Cook; Ron K. Levy; Steven M. Odre

[57] ABSTRACT

Mpl ligand analogs having one or more changed glycosylation sites as compared to a naturally occurring mpl ligand sequence of a corresponding number of amino acids are disclosed. The invention also relates to DNA sequences encoding mpl ligand analogs, recombinant plasmids and host cells for analog expression, and therapeutic compositions including such analogs.

10 Claims, 14 Drawing Sheets

| | | | |
|---|---|---|---|
| 1 | CAGGGAGCCAGCCAGCCAAGAGACACCCCGGCCAGAATGGAGCTGACTGAATTGCTCCTC | 59 | |
| -21 | | MetGluLeuThrGluLeuLeuLeu | -14 |
| 60 | GTGGTCATGCTTCTCCTAACTGCAAGGCTAGTCCAGCCCGGCTCCTCCTGCTTGT | 119 | |
| -13 | ValValMetLeuLeuLeuThrAlaArgLeuThrLeuSerSerProAlaProProAlaCys | 7 | |
| 120 | GACCTCCGAGTCCTCAGTAAACTGCTTCGTGACTCCCATGTCCTTCACAGCAGACTGAGC | 179 | |
| 8 | AspLeuArgValLeuSerLysLeuLeuArgAspSerHisValLeuHisSerArgLeuSer | 27 | |
| 180 | CAGTGCCCAGAGGTTCACCCTTGCCTACACCTGTCCTGCTGTGGACTTTAGC | 239 | |
| 28 | GlnCysProGluValHisProLeuProThrProValLeuLeuProAlaValAspPheSer | 47 | |
| 240 | TTGGGAGAATGGAAAACCCAGACTCAGATGGAGGAGACCAAGGCACAGGACATTCTGGAGCAGTG | 299 | |
| 48 | LeuGlyGluTrpLysThrGlnMetGluGluThrLysAlaGlnAspIleLeuGlyAlaVal | 67 | |
| 300 | ACCCTTCTGCTGGAGGAGTGATGGCAGCAGCGGGGACAACTGGGACCCACTTGCCTCTCA | 359 | |
| 68 | ThrLeuLeuLeuGluGluValMetAlaAlaArgGlyGlnLeuGlyProThrCysLeuSer | 87 | |
| 360 | TCCCTCCTGGGCAGCTTTCTGGACAGGTCCGTCCTCCTTGGGCCCCTGCAGAGCCTC | 419 | |
| 88 | SerLeuLeuGlyGlnLeuSerGlyGlnValArgLeuLeuLeuGlyAlaLeuGlnSerLeu | 107 | |

FIG.1A

| | | | |
|---|---|---|---|
| 420 | CTTGGAACCCAGCTTCCTCACAGGGCAGGACCACCAGCTCACAAGGATCCCAATGCCATCC | 479 |
| 108 | LeuGlyThrGlnLeuProProGlnGlyArgThrThrAlaHisLysAspProAsnAlaIle | 127 |
| 480 | TTCCTGAGCTTCCAACACCTGCTCCGAGGAAAGGTGCGTTTCCTGATGCTTGTAGGAGGG | 539 |
| 128 | PheLeuSerPheGlnHisLeuLeuArgGlyLysValArgPheLeuMetLeuValGlyGly | 147 |
| 540 | TCCACCCTCTGCGTCAGGGCCCCACCAGCTGTCCCCAGCAGAACCTCTCTA | 599 |
| 148 | SerThrLeuCysValArgArgAlaProProThrAlaValProSerArgThrSerLeu | 167 |
| 600 | GTCCTCACACTGAACGAGCTCCCAAACAGGACTTCGGATTGTTGGAGACAAACTTCACT | 659 |
| 168 | ValLeuThrLeuAsnGluLeuProAsnArgThrSerGlyLeuLeuGluThrAsnPheThr | 187 |
| 660 | GCCTCAGCCAGAACTACTGGCTTCTGAAGTGGCAGCAGGATTCAGAGCCAAG | 719 |
| 188 | AlaSerAlaArgThrThrGlySerGlyLeuLeuLysTrpGlnGlnGlyPheArgAlaLys | 207 |
| 720 | ATTCCCTGGTCGCTGAACTTGAACCAAATCCCCGATACCTGAAC | 779 |
| 208 | IleProGlyLeuLeuAsnGlnThrSerArgSerLeuAspGlnIleProGlyTyrLeuAsn | 227 |
| 780 | AGGATACACGAACTCTTGAATGGAACTCGTGGACTCTTTCCTGGACCCTCACGCAGGACC | 839 |
| 228 | ArgIleHisGluLeuLeuAsnGlyThrArgGlyLeuPheProGlyProSerArgArgThr | 247 |

FIG.1B

```
840   CTAGGAGCCCCGGACATTTCCTCAGGAACATCAGACACAGGCTCCCTGCCACCAACCTC   899
248   LeuGlyAlaProAspIleSerSerGlyThrSerAspThrGlySerLeuProProAsnLeu   267

900   CAGCCTGGATATTCCTTCCCCAACCTCCTACTGGACAGTATACGCTCTTCCCT         959
268   GlnProGlyTyrSerProSerProThrHisProProThrGlyGlnTyrThrLeuPhePro  287

960   CTTCCACCCACCTTGCCCACCCCTGTGGTCCAGCTCCACCCCCTGCTTCCTGACCCTTCT  1019
288   LeuProThrLeuProThrProValValGlnLeuHisProLeuLeuProAspProSer     307

1020  GCTCCAACGCCCCACCCCTACACCAGCCTCTAAACATCCTACACCCACTCCCAGAAT     1079
308   AlaProThrProThrProSerProLeuLeuAsnThrSerTyrThrHisSerGlnAsn      327

1080  CTGTCTCAGGAAGGGTAAGGTTCTCAGACACTGCCGACATCAGCATTGTCTCGTACAG    1139
328   LeuSerGlnGluGlyEnd                                             332
1140  CTCCCTTCCCTGCAGGGCGCCCCTGGGAGACAACTGGACAAGATTTCCTACTTTCCTG    1199
1200  AAACCCAAGCCCTGGTAAAGGGATACACAGGACTGAAAAGGGAATCATTTTCACTGT     1259
1260  ACATTATAAACCTTCAGAAGCTATTTTTTTAAGCTATCAGCAATACTACTCATCAGAGCAGCT 1319
1320  AGCTCTTTGGTCTATTTCTGCA    1342
```

FIG.1C

```
TCTAGACCACCATGGAGCTGACTGAATTGCTCCTCGTGGTCATGCTTCTCCTAACTGCAA
           M  E  L  T  E  L  L  L  V  V  M  L  L  L  T  A  R

GGCTAACGCTGTCCAGCCCCGGCTCCTCCTGTGACCTCCGAGTCCTCAGTAAACTGCTGC
 L  T  L  S  S  P  A  P  P  A  C  D  L  R  V  L  S  K  L  L

TTCGTGACTCCCACGTCCTCCACAGCAGACTGAGCCAGTGCCCAGAGGTTCACCCTTTGC
 R  D  S  H  V  L  H  S  R  L  S  Q  C  P  E  V  H  P  L  P

CTACACCTTGTCCTGCCTGCTGTGGACTTTAGCTTGGGAGAATGGAAAACCCAGATGG
 T  P  V  L  L  P  A  V  D  F  S  L  G  E  W  K  T  Q  M  E

AGGAGACCAAGGCACAGGACATTCTGGGAGCAGTGACCCTTCTGCTGGAGGGAGTGATGG
 E  T  K  A  Q  D  I  L  G  A  V  T  L  L  L  E  G  V  M  A
```

FIG. 2A

```
         310                     330                     350
CAGCACGGGGACAACTGGGACCCCACTTGCCTCTCATCCCTCCTGGGGCAGCTTTCTGGAC
 A  R  G  Q  L  G  P  T  C  L  S  S  L  L  G  Q  L  S  G  Q 370                     390                     410
AGGTCCGTCTCCTCCTTGGGGCCCTGCAGAGCCTCCTTGGAACCCAGTCTCCTCCACAGG
 V  R  L  L  L  G  A  L  Q  S  L  L  G  T  Q  L  P  P  Q  G 430                     450                     470
GCAGGACCACAGCTCACAAGGATCCCAATGCCATCTTCCTGAGCTTCCAACACCTGCTCC
 R  T  T  A  H  K  D  P  N  A  I  F  L  S  F  Q  H  L  L  R 490                     510                     530
GAGGAAAGGTGCGTTTCCTGATGCTTGTAGGAGGTCCACCCTGCGTCAGGCGGGCCC
 G  K  V  R  F  L  M  L  V  G  G  S  T  L  C  V  R  R  A  P 550                     570                     590
CACCCACCACAGCTGTCCCAGCAGAACCTCTAGTCCTCACACTGAACGAGCTCTAGG
 P  L  P  A  V  P  S  R  T  S  L  V  L  T  L  N  E  L  *

TCGAC
```

FIG. 2B

FIG.8A
FIG.8B
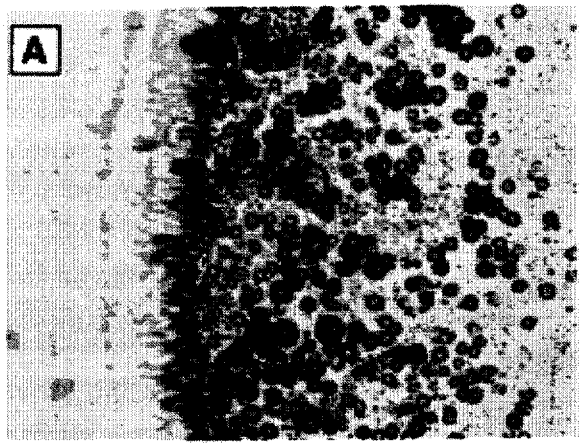
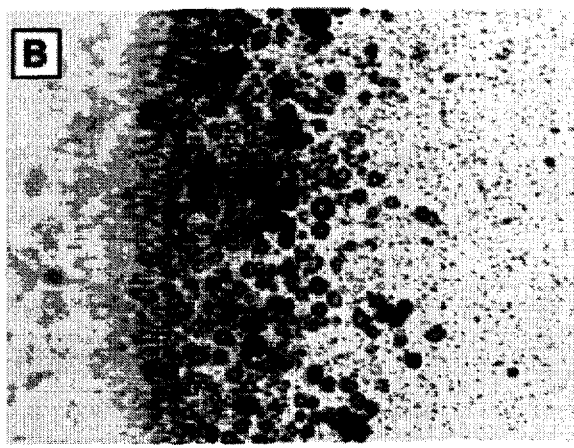
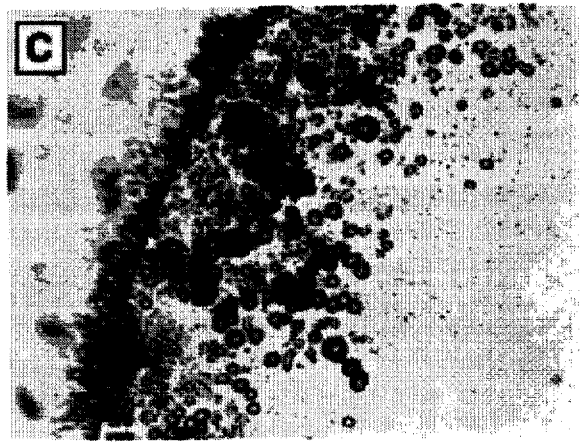
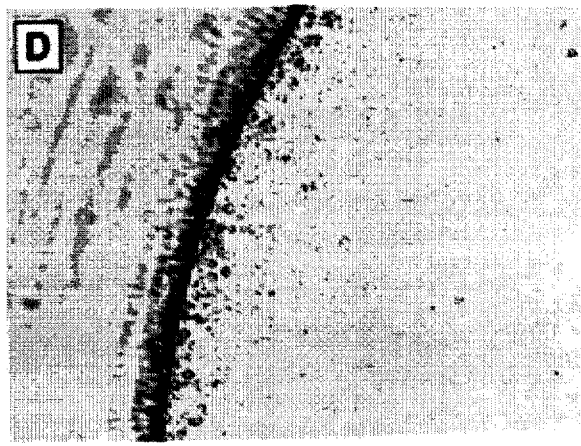
FIG.8C
FIG.8D

— ■ — 5. CHO-174-15

— ♦ — 2. CHO-1-332

— ▲ — 4. CHO-174-4

— ● — 3. CHO 1-174

— ♦ — 6. E coli Mk 1-174

— + — 1. Carrier

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 1342 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 36..1094

( i x ) FEATURE:
        ( A ) NAME/KEY: mat_peptide
        ( B ) LOCATION: 99..1094

( i x ) FEATURE:
        ( A ) NAME/KEY: sig_peptide
        ( B ) LOCATION: 36..98

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| CAGGGAGCCA | CGCCAGCCAA | GACACCCCGG | CCAGA | ATG | GAG | CTG | ACT | GAA | TTG | | | | | | | 53 |
| | | | | Met | Glu | Leu | Thr | Glu | Leu | | | | | | | |
| | | | | -21 | | | | | -20 | | | | | | | |

| CTC | CTC | GTG | GTC | ATG | CTT | CTC | CTA | ACT | GCA | AGG | CTA | ACG | CTG | TCC | AGC | 101 |
|---|---|---|---|---|---|---|---|---|---|---|---|---|---|---|---|---|
| Leu | Leu | Val | Val | Met | Leu | Leu | Leu | Thr | Ala | Arg | Leu | Thr | Leu | Ser | Ser | |
| -15 | | | | -10 | | | | | -5 | | | | | | 1 | |

| CCG | GCT | CCT | CCT | GCT | TGT | GAC | CTC | CGA | GTC | CTC | AGT | AAA | CTG | CTT | CGT | 149 |
|---|---|---|---|---|---|---|---|---|---|---|---|---|---|---|---|---|
| Pro | Ala | Pro | Pro | Ala | Cys | Asp | Leu | Arg | Val | Leu | Ser | Lys | Leu | Leu | Arg | |
| | | | 5 | | | | | 10 | | | | | 15 | | | |

| GAC | TCC | CAT | GTC | CTT | CAC | AGC | AGA | CTG | AGC | CAG | TGC | CCA | GAG | GTT | CAC | 197 |
|---|---|---|---|---|---|---|---|---|---|---|---|---|---|---|---|---|
| Asp | Ser | His | Val | Leu | His | Ser | Arg | Leu | Ser | Gln | Cys | Pro | Glu | Val | His | |
| | | 20 | | | | | 25 | | | | | 30 | | | | |

| CCT | TTG | CCT | ACA | CCT | GTC | CTG | CTG | CCT | GCT | GTG | GAC | TTT | AGC | TTG | GGA | 245 |
|---|---|---|---|---|---|---|---|---|---|---|---|---|---|---|---|---|
| Pro | Leu | Pro | Thr | Pro | Val | Leu | Leu | Pro | Ala | Val | Asp | Phe | Ser | Leu | Gly | |
| | 35 | | | | 40 | | | | | 45 | | | | | | |

| GAA | TGG | AAA | ACC | CAG | ATG | GAG | GAG | ACC | AAG | GCA | CAG | GAC | ATT | CTG | GGA | 293 |
|---|---|---|---|---|---|---|---|---|---|---|---|---|---|---|---|---|
| Glu | Trp | Lys | Thr | Gln | Met | Glu | Glu | Thr | Lys | Ala | Gln | Asp | Ile | Leu | Gly | |
| 50 | | | | | 55 | | | | 60 | | | | | | 65 | |

| GCA | GTG | ACC | CTT | CTG | CTG | GAG | GGA | GTG | ATG | GCA | GCA | CGG | GGA | CAA | CTG | 341 |
|---|---|---|---|---|---|---|---|---|---|---|---|---|---|---|---|---|
| Ala | Val | Thr | Leu | Leu | Leu | Glu | Gly | Val | Met | Ala | Ala | Arg | Gly | Gln | Leu | |
| | | | | 70 | | | | | 75 | | | | | 80 | | |

| GGA | CCC | ACT | TGC | CTC | TCA | TCC | CTC | CTG | GGG | CAG | CTT | TCT | GGA | CAG | GTC | 389 |
|---|---|---|---|---|---|---|---|---|---|---|---|---|---|---|---|---|
| Gly | Pro | Thr | Cys | Leu | Ser | Ser | Leu | Leu | Gly | Gln | Leu | Ser | Gly | Gln | Val | |
| | | | 85 | | | | | 90 | | | | | 95 | | | |

| CGT | CTC | CTC | CTT | GGG | GCC | CTG | CAG | AGC | CTC | CTT | GGA | ACC | CAG | CTT | CCT | 437 |
|---|---|---|---|---|---|---|---|---|---|---|---|---|---|---|---|---|
| Arg | Leu | Leu | Leu | Gly | Ala | Leu | Gln | Ser | Leu | Leu | Gly | Thr | Gln | Leu | Pro | |
| | | 100 | | | | | 105 | | | | | 110 | | | | |

| CCA | CAG | GGC | AGG | ACC | ACA | GCT | CAC | AAG | GAT | CCC | AAT | GCC | ATC | TTC | CTG | 485 |
|---|---|---|---|---|---|---|---|---|---|---|---|---|---|---|---|---|
| Pro | Gln | Gly | Arg | Thr | Thr | Ala | His | Lys | Asp | Pro | Asn | Ala | Ile | Phe | Leu | |
| | 115 | | | | | 120 | | | | | 125 | | | | | |

| AGC | TTC | CAA | CAC | CTG | CTC | CGA | GGA | AAG | GTG | CGT | TTC | CTG | ATG | CTT | GTA | 533 |
|---|---|---|---|---|---|---|---|---|---|---|---|---|---|---|---|---|
| Ser | Phe | Gln | His | Leu | Leu | Arg | Gly | Lys | Val | Arg | Phe | Leu | Met | Leu | Val | |
| 130 | | | | | 135 | | | | | 140 | | | | | 145 | |

| GGA | GGG | TCC | ACC | CTC | TGC | GTC | AGG | CGG | GCC | CCA | CCC | ACC | ACA | GCT | GTC | 581 |
|---|---|---|---|---|---|---|---|---|---|---|---|---|---|---|---|---|
| Gly | Gly | Ser | Thr | Leu | Cys | Val | Arg | Arg | Ala | Pro | Pro | Thr | Thr | Ala | Val | |
| | | | | 150 | | | | | 155 | | | | | 160 | | |

| CCC | AGC | AGA | ACC | TCT | CTA | GTC | CTC | ACA | CTG | AAC | GAG | CTC | CCA | AAC | AGG | 629 |
|---|---|---|---|---|---|---|---|---|---|---|---|---|---|---|---|---|
| Pro | Ser | Arg | Thr | Ser | Leu | Val | Leu | Thr | Leu | Asn | Glu | Leu | Pro | Asn | Arg | |
| | | | 165 | | | | | 170 | | | | | 175 | | | |

| ACT | TCT | GGA | TTG | TTG | GAG | ACA | AAC | TTC | ACT | GCC | TCA | GCC | AGA | ACT | ACT | 677 |
|---|---|---|---|---|---|---|---|---|---|---|---|---|---|---|---|---|
| Thr | Ser | Gly | Leu | Leu | Glu | Thr | Asn | Phe | Thr | Ala | Ser | Ala | Arg | Thr | Thr | |
| | | 180 | | | | | 185 | | | | | 190 | | | | |

| GGC | TCT | GGG | CTT | CTG | AAG | TGG | CAG | CAG | GGA | TTC | AGA | GCC | AAG | ATT | CCT | 725 |
|---|---|---|---|---|---|---|---|---|---|---|---|---|---|---|---|---|
| Gly | Ser | Gly | Leu | Leu | Lys | Trp | Gln | Gln | Gly | Phe | Arg | Ala | Lys | Ile | Pro | |
| | 195 | | | | | 200 | | | | | 205 | | | | | |

| GGT | CTG | CTG | AAC | CAA | ACC | TCC | AGG | TCC | CTG | GAC | CAA | ATC | CCC | GGA | TAC | 773 |
|---|---|---|---|---|---|---|---|---|---|---|---|---|---|---|---|---|
| Gly | Leu | Leu | Asn | Gln | Thr | Ser | Arg | Ser | Leu | Asp | Gln | Ile | Pro | Gly | Tyr | |
| 210 | | | | | 215 | | | | | 220 | | | | | 225 | |

| CTG | AAC | AGG | ATA | CAC | GAA | CTC | TTG | AAT | GGA | ACT | CGT | GGA | CTC | TTT | CCT | 821 |
|---|---|---|---|---|---|---|---|---|---|---|---|---|---|---|---|---|
| Leu | Asn | Arg | Ile | His | Glu | Leu | Leu | Asn | Gly | Thr | Arg | Gly | Leu | Phe | Pro | |
| | | | | 230 | | | | | 235 | | | | | 240 | | |

| GGA | CCC | TCA | CGC | AGG | ACC | CTA | GGA | GCC | CCG | GAC | ATT | TCC | TCA | GGA | ACA | 869 |
|---|---|---|---|---|---|---|---|---|---|---|---|---|---|---|---|---|
| Gly | Pro | Ser | Arg | Arg | Thr | Leu | Gly | Ala | Pro | Asp | Ile | Ser | Ser | Gly | Thr | |
| | | | 245 | | | | | 250 | | | | | 255 | | | |

| TCA | GAC | ACA | GGC | TCC | CTG | CCA | CCC | AAC | CTC | CAG | CCT | GGA | TAT | TCT | CCT | 917 |
|---|---|---|---|---|---|---|---|---|---|---|---|---|---|---|---|---|
| Ser | Asp | Thr | Gly | Ser | Leu | Pro | Pro | Asn | Leu | Gln | Pro | Gly | Tyr | Ser | Pro | |
| | | 260 | | | | | 265 | | | | | 270 | | | | |

| TCC | CCA | ACC | CAT | CCT | CCT | ACT | GGA | CAG | TAT | ACG | CTC | TTC | CCT | CTT | CCA | 965 |

```
Ser  Pro  Thr  His  Pro  Pro  Thr  Gly  Gln  Tyr  Thr  Leu  Phe  Pro  Leu  Pro
     275                      280                     285

CCC  ACC  TTG  CCC  ACC  CCT  GTG  GTC  CAG  CTC  CAC  CCC  CTG  CTT  CCT  GAC      1013
Pro  Thr  Leu  Pro  Thr  Pro  Val  Val  Gln  Leu  His  Pro  Leu  Leu  Pro  Asp
290                      295                     300                     305

CCT  TCT  GCT  CCA  ACG  CCC  ACC  CCT  ACC  AGC  CCT  CTT  CTA  AAC  ACA  TCC      1061
Pro  Ser  Ala  Pro  Thr  Pro  Thr  Pro  Thr  Ser  Pro  Leu  Leu  Asn  Thr  Ser
               310                     315                     320

TAC  ACC  CAC  TCC  CAG  AAT  CTG  TCT  CAG  GAA  GGG  TAAGGTTCTC  AGACACTGCC       1114
Tyr  Thr  His  Ser  Gln  Asn  Leu  Ser  Gln  Glu  Gly
               325                     330

GACATCAGCA  TTGTCTCGTG  TACAGCTCCC  TTCCCTGCAG  GGCGCCCCTG  GGAGACAACT              1174

GGACAAGATT  TCCTACTTTC  TCCTGAAACC  CAAAGCCCTG  GTAAAAGGGA  TACACAGGAC              1234

TGAAAAGGGA  ATCATTTTTC  ACTGTACATT  ATAAACCTTC  AGAAGCTATT  TTTTAAGCT               1294

ATCAGCAATA  CTCATCAGAG  CAGCTAGCTC  TTTGGTCTAT  TTTCTGCA                            1342
```

( 2 ) INFORMATION FOR SEQ ID NO:2:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Leu  Thr  Glu  Leu  Leu  Val  Val  Met  Leu  Leu  Leu  Thr  Ala
-21  -20                 -15                    -10

Arg  Leu  Thr  Leu  Ser  Ser  Pro  Ala  Pro  Pro  Ala  Cys  Asp  Leu  Arg  Val
-5                         1                    5                      10

Leu  Ser  Lys  Leu  Leu  Arg  Asp  Ser  His  Val  Leu  His  Ser  Arg  Leu  Ser
               15                     20                     25

Gln  Cys  Pro  Glu  Val  His  Pro  Leu  Pro  Thr  Pro  Val  Leu  Leu  Pro  Ala
               30                     35                     40

Val  Asp  Phe  Ser  Leu  Gly  Glu  Trp  Lys  Thr  Gln  Met  Glu  Glu  Thr  Lys
     45                     50                     55

Ala  Gln  Asp  Ile  Leu  Gly  Ala  Val  Thr  Leu  Leu  Leu  Glu  Gly  Val  Met
60                          65                     70                      75

Ala  Ala  Arg  Gly  Gln  Leu  Gly  Pro  Thr  Cys  Leu  Ser  Ser  Leu  Leu  Gly
               80                     85                     90

Gln  Leu  Ser  Gly  Gln  Val  Arg  Leu  Leu  Leu  Gly  Ala  Leu  Gln  Ser  Leu
               95                     100                    105

Leu  Gly  Thr  Gln  Leu  Pro  Pro  Gln  Gly  Arg  Thr  Thr  Ala  His  Lys  Asp
               110                    115                    120

Pro  Asn  Ala  Ile  Phe  Leu  Ser  Phe  Gln  His  Leu  Leu  Arg  Gly  Lys  Val
     125                    130                    135

Arg  Phe  Leu  Met  Leu  Val  Gly  Gly  Ser  Thr  Leu  Cys  Val  Arg  Arg  Ala
140                         145                    150                     155

Pro  Pro  Thr  Thr  Ala  Val  Pro  Ser  Arg  Thr  Ser  Leu  Val  Leu  Thr  Leu
               160                    165                    170

Asn  Glu  Leu  Pro  Asn  Arg  Thr  Ser  Gly  Leu  Leu  Glu  Thr  Asn  Phe  Thr
     175                    180                    185

Ala  Ser  Ala  Arg  Thr  Thr  Gly  Ser  Gly  Leu  Leu  Lys  Trp  Gln  Gln  Gly
     190                    195                    200

Phe  Arg  Ala  Lys  Ile  Pro  Gly  Leu  Leu  Asn  Gln  Thr  Ser  Arg  Ser  Leu
     205                    210                    215
```

```
Asp Gln Ile Pro Gly Tyr Leu Asn Arg Ile His Glu Leu Leu Asn Gly
220                 225                 230                 235

Thr Arg Gly Leu Phe Pro Gly Pro Ser Arg Arg Thr Leu Gly Ala Pro
                240                 245                 250

Asp Ile Ser Ser Gly Thr Ser Asp Thr Gly Ser Leu Pro Pro Asn Leu
            255                 260                 265

Gln Pro Gly Tyr Ser Pro Ser Pro Thr His Pro Pro Thr Gly Gln Tyr
        270                 275                 280

Thr Leu Phe Pro Leu Pro Pro Thr Leu Pro Thr Pro Val Val Gln Leu
    285                 290                 295

His Pro Leu Leu Pro Asp Pro Ser Ala Pro Thr Pro Thr Pro Thr Ser
300                 305                 310                 315

Pro Leu Leu Asn Thr Ser Tyr Thr His Ser Gln Asn Leu Ser Gln Glu
                320                 325                 330

Gly
```

( 2 ) INFORMATION FOR SEQ ID NO:3:

( i ) SEQUENCE CHARACTERISTICS:
        ( A ) LENGTH: 605 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 12..596

( i x ) FEATURE:
        ( A ) NAME/KEY: mat_peptide
        ( B ) LOCATION: 75..596

( i x ) FEATURE:
        ( A ) NAME/KEY: sig_peptide
        ( B ) LOCATION: 12..74

( x i ) SEQUENCE DESCRIPTION: SEQ ID NO:3:

```
TCTAGACCAC C ATG GAG CTG ACT GAA TTG CTC CTC GTG GTC ATG CTT CTC        50
             Met Glu Leu Thr Glu Leu Leu Leu Val Val Met Leu Leu
             -21 -20             -15                      -10

CTA ACT GCA AGG CTA ACG CTG TCC AGC CCG GCT CCT CCT GCT TGT GAC         98
Leu Thr Ala Arg Leu Thr Leu Ser Ser Pro Ala Pro Pro Ala Cys Asp
             -5                  1                   5

CTC CGA GTC CTC AGT AAA CTG CTT CGT GAC TCC CAC GTC CTT CAC AGC         146
Leu Arg Val Leu Ser Lys Leu Leu Arg Asp Ser His Val Leu His Ser
        10                  15                  20

AGA CTG AGC CAG TGC CCA GAG GTT CAC CCT TTG CCT ACA CCT GTC CTG         194
Arg Leu Ser Gln Cys Pro Glu Val His Pro Leu Pro Thr Pro Val Leu
25                  30                  35                  40

CTG CCT GCT GTG GAC TTT AGC TTG GGA GAA TGG AAA ACC CAG ATG GAG         242
Leu Pro Ala Val Asp Phe Ser Leu Gly Glu Trp Lys Thr Gln Met Glu
                45                  50                  55

GAG ACC AAG GCA CAG GAC ATT CTG GGA GCA GTG ACC CTT CTG CTG GAG         290
Glu Thr Lys Ala Gln Asp Ile Leu Gly Ala Val Thr Leu Leu Leu Glu
            60                  65                  70

GGA GTG ATG GCA GCA CGG GGA CAA CTG GGA CCC ACT TGC CTC TCA TCC         338
Gly Val Met Ala Ala Arg Gly Gln Leu Gly Pro Thr Cys Leu Ser Ser
        75                  80                  85

CTC CTG GGG CAG CTT TCT GGA CAG GTC CGT CTC CTC CTT GGG GCC CTG         386
Leu Leu Gly Gln Leu Ser Gly Gln Val Arg Leu Leu Leu Gly Ala Leu
        90                  95                  100
```

```
CAG  AGC  CTC  CTT  GGA  ACC  CAG  CTT  CCT  CCA  CAG  GGC  AGG  ACC  ACA  GCT    434
Gln  Ser  Leu  Leu  Gly  Thr  Gln  Leu  Pro  Pro  Gln  Gly  Arg  Thr  Thr  Ala
105                           110                 115                      120

CAC  AAG  GAT  CCC  AAT  GCC  ATC  TTC  CTG  AGC  TTC  CAA  CAC  CTG  CTC  CGA    482
His  Lys  Asp  Pro  Asn  Ala  Ile  Phe  Leu  Ser  Phe  Gln  His  Leu  Leu  Arg
                    125                      130                      135

GGA  AAG  GTG  CGT  TTC  CTG  ATG  CTT  GTA  GGA  GGG  TCC  ACC  CTC  TGC  GTC    530
Gly  Lys  Val  Arg  Phe  Leu  Met  Leu  Val  Gly  Gly  Ser  Thr  Leu  Cys  Val
               140                      145                      150

AGG  CGG  GCC  CCA  CCC  ACC  ACA  GCT  GTC  CCC  AGC  AGA  ACC  TCT  CTA  GTC    578
Arg  Arg  Ala  Pro  Pro  Thr  Thr  Ala  Val  Pro  Ser  Arg  Thr  Ser  Leu  Val
          155                      160                      165

CTC  ACA  CTG  AAC  GAG  CTC  TAGGTCGAC                                             605
Leu  Thr  Leu  Asn  Glu  Leu
          170
```

( 2 ) INFORMATION FOR SEQ ID NO:4:

( i ) SEQUENCE CHARACTERISTICS:
    ( A ) LENGTH: 195 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met  Glu  Leu  Thr  Glu  Leu  Leu  Val  Val  Met  Leu  Leu  Leu  Thr  Ala
-21       -20                 -15                 -10

Arg  Leu  Thr  Leu  Ser  Ser  Pro  Ala  Pro  Ala  Cys  Asp  Leu  Arg  Val
-5                       1                 5                      10

Leu  Ser  Lys  Leu  Leu  Arg  Asp  Ser  His  Val  Leu  His  Ser  Arg  Leu  Ser
               15                      20                      25

Gln  Cys  Pro  Glu  Val  His  Pro  Leu  Pro  Thr  Pro  Val  Leu  Leu  Pro  Ala
               30                      35                      40

Val  Asp  Phe  Ser  Leu  Gly  Glu  Trp  Lys  Thr  Gln  Met  Glu  Glu  Thr  Lys
     45                      50                      55

Ala  Gln  Asp  Ile  Leu  Gly  Ala  Val  Thr  Leu  Leu  Leu  Glu  Gly  Val  Met
60                       65                      70                       75

Ala  Ala  Arg  Gly  Gln  Leu  Gly  Pro  Thr  Cys  Leu  Ser  Ser  Leu  Leu  Gly
                    80                      85                       90

Gln  Leu  Ser  Gly  Gln  Val  Arg  Leu  Leu  Leu  Gly  Ala  Leu  Gln  Ser  Leu
               95                      100                     105

Leu  Gly  Thr  Gln  Leu  Pro  Pro  Gln  Gly  Arg  Thr  Thr  Ala  His  Lys  Asp
               110                     115                     120

Pro  Asn  Ala  Ile  Phe  Leu  Ser  Phe  Gln  His  Leu  Leu  Arg  Gly  Lys  Val
     125                     130                     135

Arg  Phe  Leu  Met  Leu  Val  Gly  Gly  Ser  Thr  Leu  Cys  Val  Arg  Arg  Ala
140                      145                     150                     155

Pro  Pro  Thr  Thr  Ala  Val  Pro  Ser  Arg  Thr  Ser  Leu  Val  Leu  Thr  Leu
               160                     165                     170

Asn  Glu  Leu
```

( 2 ) INFORMATION FOR SEQ ID NO:5:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( A ) DESCRIPTION: /desc = "nucleic acid"

( x i ) SEQUENCE DESCRIPTION: SEQ ID NO:5:

CCCATGTCAA TCACAGCAGA CT 22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:6:

CTTCACAGCA ACCTGAGCCA GT 22

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:7:

CAGTGCAACG AGACCCACCC TTTG 24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:8:

GCCTACAAAT GTCACGCTGC CTGCT 25

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:9:

CCCACTTGTA ACTCATCCCT C 21

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: /desc = "nucleic acid"

(x i) SEQUENCE DESCRIPTION: SEQ ID NO:10:

CAACTGAACG CCACTTGTCT CTCA                                                                24

(2) INFORMATION FOR SEQ ID NO:11:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (i i) MOLECULE TYPE: other nucleic acid
      (A) DESCRIPTION: /desc = "nucleic acid"

(x i) SEQUENCE DESCRIPTION: SEQ ID NO:11:

ACTTGTCTCA ACTCCACCCT GGGGGA                                                              26

(2) INFORMATION FOR SEQ ID NO:12:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: other nucleic acid
      (A) DESCRIPTION: /desc = "nucleic acid"

(x i) SEQUENCE DESCRIPTION: SEQ ID NO:12:

CTCCTGGGGA ACCTTTCTGG A                                                                   21

(2) INFORMATION FOR SEQ ID NO:13:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (i i) MOLECULE TYPE: other nucleic acid
      (A) DESCRIPTION: /desc = "nucleic acid"

(x i) SEQUENCE DESCRIPTION: SEQ ID NO:13:

GACCACAAAT CACACCGATC CCAAT                                                               25

(2) INFORMATION FOR SEQ ID NO:14:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (i i) MOLECULE TYPE: other nucleic acid
      (A) DESCRIPTION: /desc = "nucleic acid"

(x i) SEQUENCE DESCRIPTION: SEQ ID NO:14:

ACCCTTTGTC TACAAATGTC ACGCTGCCTG CT                                                       32

(2) INFORMATION FOR SEQ ID NO:15:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (i i) MOLECULE TYPE: other nucleic acid ( A ) DESCRIPTION: /desc = "nucleic acid"

( x i ) SEQUENCE DESCRIPTION: SEQ ID NO:15:

TCTCTCAAAC CTCACGGGGG AGCTT                                    25

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:16:

TGGAAAAATC AGACGGAGGA GAC                                      23

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:17:

TGGAGGAGAA CAAGACACAG GACAT                                    25

( 2 ) INFORMATION FOR SEQ ID NO:18:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:18:

CCCTCTAGAC CACCATGGAA CTGACTGAAT TGCTCCTC                      38

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..28)

( x i ) SEQUENCE DESCRIPTION: SEQ ID NO:19:

GTGTGACTTG CTCGAGACTC AGCTGCCC                                 28

( 2 ) INFORMATION FOR SEQ ID NO:20:

( i ) SEQUENCE CHARACTERISTICS:
        ( A ) LENGTH: 29 base pairs
        ( B ) TYPE: nucleic acid ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..29)

( x i ) SEQUENCE DESCRIPTION: SEQ ID NO:20:

GAAGACCTAA CAACCTCACT CAGCTGCCC 29

( 2 ) INFORMATION FOR SEQ ID NO:21:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..29)

( x i ) SEQUENCE DESCRIPTION: SEQ ID NO:21:

AGTGACGGAG TCGGTCTATT CAGCTGCCC 29

( 2 ) INFORMATION FOR SEQ ID NO:22:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:22:

CACGTCCTTA ACAGCAGCCT GAGCCAGTG 29

( 2 ) INFORMATION FOR SEQ ID NO:23:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..29)

( x i ) SEQUENCE DESCRIPTION: SEQ ID NO:23:

GTGCAGGAAT TGTCGTCGGA CTCGGTCAC 29

( 2 ) INFORMATION FOR SEQ ID NO:24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "nucleic acid"

( x i ) SEQUENCE DESCRIPTION: SEQ ID NO:24:

CCCTTTGCCT AACGGTTCCC TGCTGCCTGC TGT  33

( 2 ) INFORMATION FOR SEQ ID NO:25:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..33)

( x i ) SEQUENCE DESCRIPTION: SEQ ID NO:25:

GGGAAACGGA TTGCCAAGGG ACGACGGACG ACA  33

( 2 ) INFORMATION FOR SEQ ID NO:26:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:26:

TGCCTACACC TAACCTGTCG CCTGCTGTGG A  31

( 2 ) INFORMATION FOR SEQ ID NO:27:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..31)

( x i ) SEQUENCE DESCRIPTION: SEQ ID NO:27:

ACGGATGTGG ATTGGACAGC GGACGACACC T  31

( 2 ) INFORMATION FOR SEQ ID NO:28:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:28:

GGAAAACCAA TATGTCGGAG ACCAAGGCAC A  31

( 2 ) INFORMATION FOR SEQ ID NO:29:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( i x ) FEATURE:
    ( A ) NAME/KEY: -
    ( B ) LOCATION: complement (1..31)

( x i ) SEQUENCE DESCRIPTION: SEQ ID NO:29:

```
CCTTTTGGTT ATACAGCCTC TGGTTCCGTG T                                         31
```

( 2 ) INFORMATION FOR SEQ ID NO:30:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( x i ) SEQUENCE DESCRIPTION: SEQ ID NO:30:

```
TGGGAGAATG GAACACCACG ATGGAGGAGA CC                                        32
```

( 2 ) INFORMATION FOR SEQ ID NO:31:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( i x ) FEATURE:
    ( A ) NAME/KEY: -
    ( B ) LOCATION: complement (1..32)

( x i ) SEQUENCE DESCRIPTION: SEQ ID NO:31:

```
ACCCTCTTAC CTTGTGGTGC TACCTCCTCT GG                                        32
```

( 2 ) INFORMATION FOR SEQ ID NO:32:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( x i ) SEQUENCE DESCRIPTION: SEQ ID NO:32:

```
AAAACCCAGA TGAACGAGAC GACCAAGGCA CA                                        32
```

( 2 ) INFORMATION FOR SEQ ID NO:33:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid ( A ) DESCRIPTION: /desc = "nucleic acid"

( i x ) FEATURE:
    ( A ) NAME/KEY: -
    ( B ) LOCATION: complement (1..32)

( x i ) SEQUENCE DESCRIPTION: SEQ ID NO:33:

```
TTTGGGTCT  ACTTGCTCTG  CTGGTTCCGT  GT                                    3 2
```

( 2 ) INFORMATION FOR SEQ ID NO:34:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( x i ) SEQUENCE DESCRIPTION: SEQ ID NO:34:

```
CCCAGATGGA  GAACACCTCG  GCACAGGACA  T                                    3 1
```

( 2 ) INFORMATION FOR SEQ ID NO:35:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( i x ) FEATURE:
    ( A ) NAME/KEY: -
    ( B ) LOCATION: complement (1..31)

( x i ) SEQUENCE DESCRIPTION: SEQ ID NO:35:

```
GGGTCTACCT  CTTGTGGAGC  CGTGTCCTGT  A                                    3 1
```

( 2 ) INFORMATION FOR SEQ ID NO:36:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( x i ) SEQUENCE DESCRIPTION: SEQ ID NO:36:

```
CACGGGGACA  AAACGGAACC  ACTTGCCTCT  CA                                   3 2
```

( 2 ) INFORMATION FOR SEQ ID NO:37:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "nucleic acid"

( i x ) FEATURE:
    ( A ) NAME/KEY: -
    ( B ) LOCATION: complement (1..32)

( x i ) SEQUENCE DESCRIPTION: SEQ ID NO:37:

GTGCCCCTGT TTTGCCTTGG TGAACGGAGA GT 32

( 2 ) INFORMATION FOR SEQ ID NO:38:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:38:

CAGGGCAGGA ACACATCTCA CAAGGATCCC A 31

( 2 ) INFORMATION FOR SEQ ID NO:39:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..31)

( x i ) SEQUENCE DESCRIPTION: SEQ ID NO:39:

GTCCCGTCCT TGTGTAGAGT GTTCCTAGGG T 31

( 2 ) INFORMATION FOR SEQ ID NO:40:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:40:

GGGCAGGACC AACGCTAGCA AGGATCCCAA T 31

( 2 ) INFORMATION FOR SEQ ID NO:41:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..31)

( x i ) SEQUENCE DESCRIPTION: SEQ ID NO:41:

CCCGTCCTGG TTGCGATCGT TCCTAGGGTT A 31

( 2 ) INFORMATION FOR SEQ ID NO:42:

( i ) SEQUENCE CHARACTERISTICS:
        ( A ) LENGTH: 24 base pairs
        ( B ) TYPE: nucleic acid ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:42:

CAGTGCAACG AGTCCCACCC TTGG 24

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..24)

( x i ) SEQUENCE DESCRIPTION: SEQ ID NO:43:

GTCACGTTGC TCAGGGTGGG AAAC 24

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:44:

GACCACAAAT CACTCCGATC CCAA 24

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..24)

( x i ) SEQUENCE DESCRIPTION: SEQ ID NO:45:

CTGGTGTTTA GTGAGGCTAG GGTT 24

( 2 ) INFORMATION FOR SEQ ID NO:46:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:46:

```
GTCCCCACCA ACACCTCTCT AGTCCTC                                                    27
```

( 2 ) INFORMATION FOR SEQ ID NO:47:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..27)

( x i ) SEQUENCE DESCRIPTION: SEQ ID NO:47:

```
CAGGGGTGGT TGTGGAGAGA TCAGGAG                                                    27
```

( 2 ) INFORMATION FOR SEQ ID NO:48:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..33)

( x i ) SEQUENCE DESCRIPTION: SEQ ID NO:48:

```
TGACCGAGAC CCGAAGACTT CACTCAGCTG CCC                                             33
```

( 2 ) INFORMATION FOR SEQ ID NO:49:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( x i ) SEQUENCE DESCRIPTION: SEQ ID NO:49:

```
GAAAACCCAG AACGAGACCA CCAAGGCACA G                                               31
```

( 2 ) INFORMATION FOR SEQ ID NO:50:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "nucleic acid"

( i x ) FEATURE:
        ( A ) NAME/KEY: -
        ( B ) LOCATION: complement (1..31)

( x i ) SEQUENCE DESCRIPTION: SEQ ID NO:50:

```
CTTTTGGGTC TTGCTCTGGT GGTTCCGTGT C                                               31
```

( 2 ) INFORMATION FOR SEQ ID NO:51:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "nucleic acid"

( x i ) SEQUENCE DESCRIPTION: SEQ ID NO:51:

CACCAAGGCA CAGGACATTC TGGGAG      26

( 2 ) INFORMATION FOR SEQ ID NO:52:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "nucleic acid"

( i x ) FEATURE:
  ( A ) NAME/KEY: -
  ( B ) LOCATION: complement (1..26)

( x i ) SEQUENCE DESCRIPTION: SEQ ID NO:52:

GTGGTTCCGT GTCCTGTAAG ACCCTC      26

( 2 ) INFORMATION FOR SEQ ID NO:53:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "nucleic acid"

( x i ) SEQUENCE DESCRIPTION: SEQ ID NO:53:

GAAAACCCAG ATGAACGAGA CCAAGGCACA G      31

( 2 ) INFORMATION FOR SEQ ID NO:54:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "nucleic acid"

( i x ) FEATURE:
  ( A ) NAME/KEY: -
  ( B ) LOCATION: complement (1..31)

( x i ) SEQUENCE DESCRIPTION: SEQ ID NO:54:

CTTTTGGGTC TACTTGCTCT GGTTCCGTGT C      31

( 2 ) INFORMATION FOR SEQ ID NO:55:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: other nucleic acid (A) DESCRIPTION: /desc = "nucleic acid"

(xi) SEQUENCE DESCRIPTION: SEQ ID NO:55:

GTCCCCACCA ACACCACTCT AGTCCTC                                    27

(2) INFORMATION FOR SEQ ID NO:56:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "nucleic acid"

(ix) FEATURE:
        (A) NAME/KEY: -
        (B) LOCATION: complement (1..27)

(xi) SEQUENCE DESCRIPTION: SEQ ID NO:56:

CAGGGGTGGT TGTGGTGAGA TCAGGAG                                    27

MPL LIGAND ANALOGS

CROSS-REFERENCES

This application is a continuation-in-part of U.S. Ser. No. 08/388,779, filed Feb. 15, 1995 now U.S. Pat. No. 5,696,250.

FIELD OF THE INVENTION

The present invention relates to mpl ligand analogs having at least one changed O- or N-linked glycosylation site. The invention also relates to DNA sequences encoding these mpl ligand analogs, and recombinant plasmids and host cells for analog expression.

BACKGROUND OF THE INVENTION

MGDF, or megakaryocyte growth and development factor, is a recently cloned cytokine that appears to be the major regulator of circulating platelet levels. See Bartley, T. D. et al., Cell 77:1117–1124 (1994); Lok, S. et al., Nature 369:565–568 (1994); de Sauvage, F. J. et al., Nature 369:533–538 (1994); Miyazake, H. et al., Exp. Hematol. 22:838 (1994); and Kuter, D. J. et al., PNAS USA, 91:11104–11108 (1994). MGDF as described in Bartley, T. D. et al., Cell 77:1117–1124 (1994), is also referred to as thrombopoietin (TPO), mpl ligand, and megapoietin. Herein, the term "mpl ligand" will be used generically to refer to all polypeptides that activate the mpl receptor, including TPO and MGDF. The mpl receptor is a cell surface protein that, upon activation, leads to production and/or development of megakaryocytes and platelets. See WO 92/07074.

"Mpl ligand analogs" are polypeptides that differ from native sequences in a way that affects the number, location or type of carbohydrate linkage sites. Such polypeptides are one aspect of the present invention. Mature native human mpl ligand is a protein having 332 amino acids in total. The sequence of this protein (attached to a 21-amino acid long leader sequence) and the corresponding cDNA are shown in FIG. 1 herein (SEQ. ID NOs.: 1 and 2).

Recombinant mpl ligand produced in both Chinese Hamster Ovary (CHO) and E. coli cells has been demonstrated to have a biological activity of specifically stimulating or increasing megakaryocytes and/or platelets in vivo in mice, rats and monkeys. See e.g., Hunt, P. et al., Blood 84(10):390A (1994). Human mpl ligand molecules that have been truncated (as compared to the 332 amino acid protein encoded by the cDNA in humans) so that they extend at least 151 amino acids, starting from amino acid position 22 in FIG. 1, retain biological activity in vivo. FIG. 2 (SEQ. ID NOs.: 3 and 4) shows one example of a truncated mpl ligand molecule which, in mature form, has 174 amino acids and has biological activity. In FIG. 2, the 174 amino acid long protein is shown attached to a 21 amino acid N-terminal leader sequence. This molecule was used to create some of the mpl ligand analogs in the examples section below. Other analogs are based on amino acids 1-199, 1-191, and 1-183 of FIG. 1. It is also possible to remove up to the first six amino acids at the N-terminus of the mature human sequence mpl ligand protein and retain biological activity. Therefore, it appears that biological activity is retained within amino acids 7 to 151 (inclusive) of the mature amino acid sequence of human mpl ligand shown in FIG. 1.

In general, many cell surface and secretory proteins produced by eukaryotic cells are modified with one or more oligosaccharide groups. This modification, referred to as glycosylation, can dramatically affect the physical properties of proteins and can also be important in protein stability, secretion, and subcellular localization. Proper glycosylation can be essential for biological activity. In fact, some genes from eukaryotic organisms, when expressed in bacteria (e.g., E. coli) which lack cellular processes for glycosylating proteins, yield proteins that are recovered with little or no activity by virtue of their lack of glycosylation.

Glycosylation occurs at specific locations or sites along the polypeptide backbone and is usually of two types: O-linked oligosaccharides are attached to serine (Ser) or threonine (Thr) residues while N-linked oligosaccharides (chains) are attached to asparagine (Asn) residues when they are part of the sequence Asn-X-Ser/Thr, where X can be any amino acid except proline. X is preferably one of the 19 naturally occurring amino acids not counting proline. The structures of N-linked and O-linked oligosaccharides and the sugar residues found in each type are different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

As used herein glycosylation "sites" are amino acid residues that are structurally able to link to glycosyl residues, although such sites may or may not be actually linked to a glycosyl residue. As noted above, O-linked sites are either Ser or Thr residues, whereas N-linked sites are either Asn-X-Ser or Asn-X-Thr, where X is defined as any amino acid other than Pro (preferably one of the 19 naturally-occurring amino acids, excluding Pro). Whether a given site is glycosylated with a glycosyl chain is determined by the host cell in which the molecule is expressed, the amino acids neighboring the site, and other factors.

As used herein, the number of "chains" attached to a given mpl ligand analog will be the average number of carbohydrate (i.e., glycosyl) chains attached to a given mpl ligand molecule expressed by a particular host cell. Notably, the glycosylation sites for natural and corresponding recombinant mpl ligand will generally be the same, whereas the number of chains will possibly vary depending upon whether the particular host cell used for recombinant expression attaches glycosyl chains to the same sites or not, as compared to the natural source. Herein, whenever a comparison is made between recombinant and natural mpl ligand analogs, the same number of amino acids will be compared, regardless of whether the natural source actually produces an mpl ligand molecule having that length. Thus, "natural" refers to the sequence employed in a particular species (such as human) rather than the length of the molecule actually expressed in such natural source.

Naturally occurring mpl ligand is a glycosylated molecule. The glycosylation pattern of natural mpl ligand is related to two key domains that have been found in mpl ligand. The sequence of the first approximately 151 amino acids of mature human mpl ligand, corresponding to an active portion of the molecule, bears notable homology to erythropoietin (EPO), a cytokine capable of stimulating production of erythrocytes, and is referred to as the "EPO-like" domain of human mpl ligand. The remaining amino acids of the mature protein make up a so-called "N-linked carbohydrate" domain, since they include most if not all of the natural sites for N-linked glycosylation. In human mpl ligand, there are six N-linked glycosylation sites all contained in the N-linked glycosylation domain. Both domains contain O-linked glycosylation sites. There are an estimated 12–14 O-linked glycosylation chains in the molecule.

Experimental evidence with human mpl ligand DNA expressed recombinantly in CHO cells reveals that in the EPO-like domain at least two O-linked sites are glycosylated, at positions 1 (Ser) and 37 (Thr).

Glycoproteins such as mpl ligand can be separated into different charged forms using techniques such as isoelectric focusing (IEF). For example, several parties have reported IEF studies of crude and partially purified erythropoietin preparations (Lukowsky et al., *J. Biochem.* 50:909 (1972); Shelton et al., *Biochem. Med.* 12:45 (1975); Fuhr et al., *Biochem. Biophys. Res. Comm.* 98:930 (1981)).

In spite of the above information on glycosylation of mpl ligand molecules, there remains a need to obtain mpl ligand molecules having a different glycosylation pattern and which retain or have improved biological activity.

Accordingly, it is an object of the present invention to provide novel glycosylated mpl ligand molecules, referred to as mpl ligand analogs. It is a further object of this invention to provide pharmaceutical compositions containing such molecules and methods of treating conditions treatable by mpl ligand with the mpl ligand analogs of this invention.

SUMMARY OF THE INVENTION

In one embodiment, the subject invention relates to analogs of mpl ligand comprising an amino acid sequence which includes at least one added, at least one deleted, and/or a combination of at least one added and deleted, site for glycosylation as compared to the corresponding natural sequence mpl ligand. The added or deleted site(s) for glycosylation may result in a greater or lesser number of carbohydrate chains, and higher or lower sialic acid content, than corresponding natural sequence mpl ligand, particularly human mpl ligand. For example, one type of analog could involve deleting one or more N- or O-linked sites, and addition of one or more N- or O-linked sites at the same or another position.

In another aspect of the above embodiment, the subject invention relates to mpl ligand analogs comprising amino acid sequences which involve replacement of one or more N- or O-linked glycosylation sites with one or more non-naturally occurring sites. Thus, an N-linked site may be replaced with a different N-linked site; an N-linked site may be replaced with an O-linked site; an O-linked site may be replaced with a different O-linked site; and an O-linked site may be replaced with an N-linked site.

Combinations of any of the above changes are further encompassed within this invention.

The invention further encompasses DNA sequences encoding such mpl ligand analogs, and recombinant plasmids and host cells for analog expression.

In all of the above cases, the change in glycosylation site results in a change in the number, amount, location or type (N- vs. O-) of glycosyl chains in the resulting mpl ligand analog and retains a biological activity of mpl ligand, i.e., the analog can still activate the mpl receptor. Activation of the mpl receptor means that megakaryocytopoiesis is enhanced thereby resulting in an increase in platelets in vivo.

BRIEF DESCRIPTION OF THE DRAWINGS

FIG. 1 shows the DNA and amino acid sequence of native human mpl ligand including a signal peptide (amino acids −21 to −1) and the mature amino acid sequence (1-332).

FIG. 2 shows the DNA and amino acid sequence of mpl ligand corresponding to amino acids 1-174 of the human mature mpl ligand sequence attached to a 21 amino acid long signal peptide. The sequences flanking the coding regions have introduced XbaI and SalI cloning sites at the 5' and 3' ends respectively.

FIG. 8 shows the results of a human megakaryocyte growth bioassay with mpl ligand analogs. Panels A and D are the positive and negative controls respectively. The well pictured in panel A received 37.5 pg of wild type (i.e., natural sequence) mpl ligand 1-174 COS-1 conditioned medium and shows substantial megakaryocyte growth. Panel D received 1.5 ul of COS-1 mock conditioned medium and shows no growth. Panels B and C are mpl ligand 1-174 analogs 7 and 10 respectively. Panel B received 9.0 pg of mpl ligand COS-1 conditioned medium while panel C received 27 pg and both show excellent megakaryocyte growth.

DETAILED DESCRIPTION OF THE INVENTION

Figure 3:
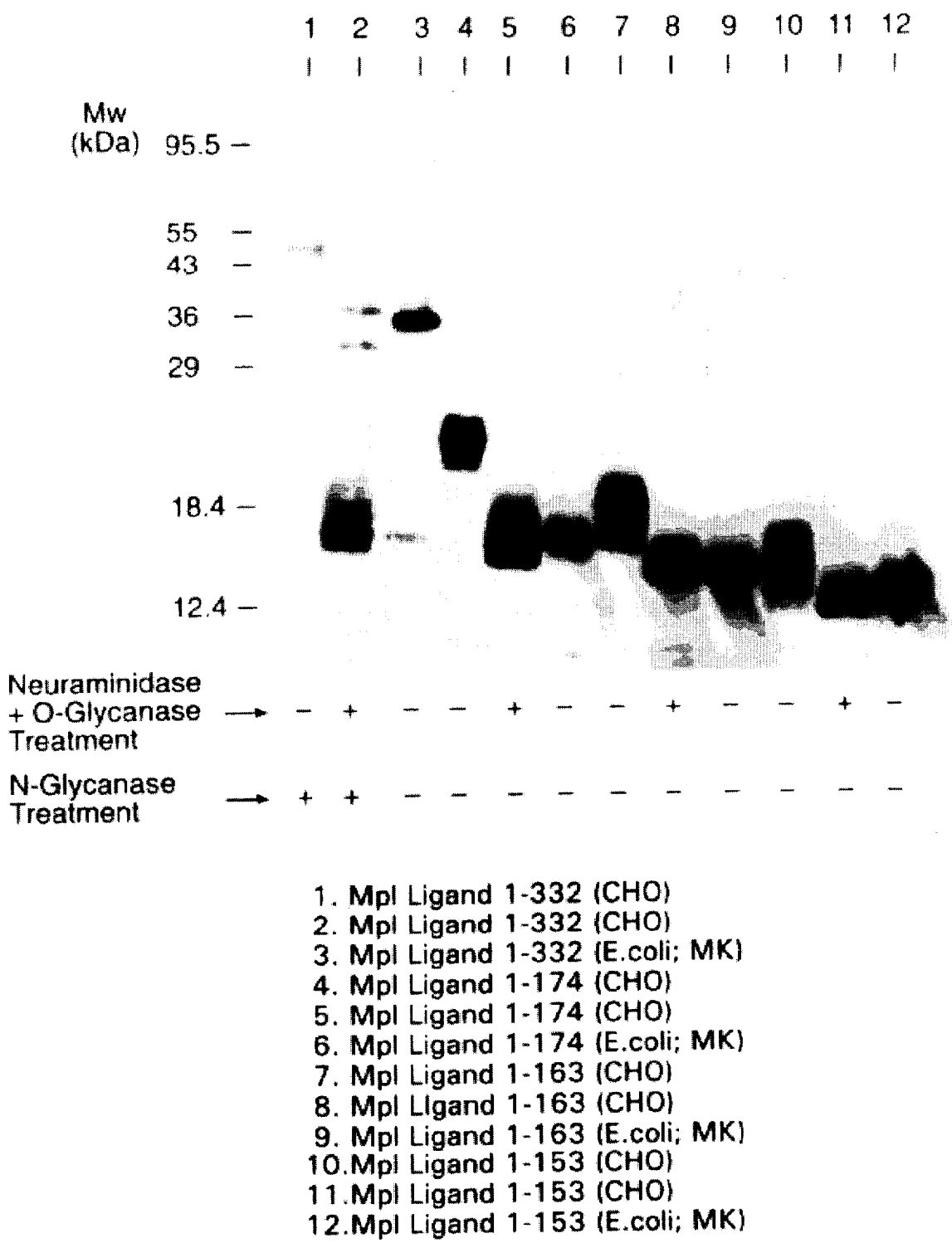
FIG. 3 shows a Western blot with *E. coli* and CHO expressed mpl ligand. MK stands for Met-Lys, which is added to the N-terminus of mpl ligand for expression in *E. coli*, and may be cleaved off using a dipeptidase, such as cathepsin C. A molecule in which MK has been removed is referred to as desMK. Treatment with the glycosidases neuraminidase and O-glycanase is indicated.

The subject invention provides mpl ligands with different glycosylation sites as compared to natural mpl ligand having a corresponding sequence. Preferably, the resulting molecules are those having additional glycosylation sites that are occupied by glycosyl chains upon expression in a mammalian cell (such as COS, CHO, and human cells).

In a first embodiment, the subject invention relates to analogs of mpl ligand comprising an amino acid sequence which includes at least one added, at least one deleted, and/or at least one added and deleted, site for glycosylation as compared to corresponding natural sequence mpl ligand. The added or deleted site(s) for glycosylation may result in a greater or lesser number of carbohydrate chains, and higher or lower sialic acid content, than corresponding natural sequence mpl ligand, particularly human mpl ligand. A combination of a deletion of one site and addition of another site would result in no net change in the number of sites, but rather, a change in location and/or type of site. Such combined change analogs are also encompassed within this invention.

In another aspect of the above embodiment, the subject invention relates to mpl ligand analogs comprising amino acid sequences which include replacement of one or more N- or O-linked glycosylation sites with one or more non-naturally occurring sites. Thus, an N-linked site may be replaced with a different N-linked site; an N-linked site may be replaced with an O-linked site; an O-linked site may be replaced with a different O-linked site; and/or an O-linked site may be replaced with an N-linked site. Replacement of one site with another site in essentially the same location may have the result of increasing the glycosylation efficiency at that site, or other effects. For example, evidence is provided herein that a Thr residue instead of a Ser residue may increase the glycosylation efficiency at O-linked sites.

The term "mpl ligand", as used herein, includes naturally occurring mpl ligand, truncations of naturally occurring mpl ligand as well as non-naturally occurring polypeptides having an amino acid sequence and glycosylation sufficiently duplicative of that of naturally occurring mpl ligand to allow possession of a biological activity of specifically stimulating growth, development and/or production of megakaryocytes and/or platelets. Mpl ligand analogs based on at least amino acids 7-151 up to amino acids 1-332 of FIG. 1 are preferred.

In a preferred embodiment, mpl ligand is the product of the expression of an exogenous DNA sequence that has been transfected into a eukaryotic host cell; that is, in a preferred embodiment the mpl ligand is "recombinant mpl ligand". The preferred eukaryotic host is mammalian, particularly preferably CHO cells. Recombinant mpl ligand is advantageously produced according to the procedures described herein and in the publications cited herein regarding cloning and expression of mpl ligand.

Some additional preferred mpl ligand molecules have the following amino acid sequences, based on FIG. 1 herein:

| mpl ligand 1-332 | amino acids 1-332 of FIG. 1 |
| mpl ligand 1-199 | amino acids 1-199 of FIG. 1 |
| mpl ligand 1-191 | amino acids 1-191 of FIG. 1 |
| mpl ligand 1-183 | amino acids 1-183 of FIG. 1 |
| mpl ligand 1-174 | amino acids 1-174 of FIG. 1 |
| mpl ligand 1-163 | amino acids 1-163 of FIG. 1 |
| mpl ligand 1-153 | amino acids 1-153 of FIG. 1 |
| mpl ligand 1-152 | amino acids 1-152 of FIG. 1 |
| mpl ligand 1-151 | amino acids 1-151 of FIG. 1 |
| mpl ligand 7-332 | amino acids 7-332 of FIG. 1 |
| mpl ligand 7-199 | amino acids 7-199 of FIG. 1 |
| mpl ligand 7-191 | amino acids 7-191 of FIG. 1 |
| mpl ligand 7-183 | amino acids 7-183 of FIG. 1 |
| mpl ligand 7-174 | amino acids 7-174 of FIG. 1 |
| mpl ligand 7-163 | amino acids 7-163 of FIG. 1 |
| mpl ligand 7-153 | amino acids 7-153 of FIG. 1 |
| mpl ligand 7-152 | amino acids 7-152 of FIG. 1 |
| mpl ligand 7-151 | amino acids 7-151 of FIG. 1 |

It should be noted, for example, that mpl ligand 1-183, 1-191, 7-183, and 7-191 encompass one or two additional naturally-occurring glycosylation sites on the C-terminus thereof, as compared to shorter sequences. In each of the above cases, Met-Lys may further be included in the N-terminus thereof.

The in vitro specific activities referred to herein are measurements of relative in vitro specific activities and are not measurements of absolute in vitro specific activities. For the purposes of this application, the specific activities are used only to compare relative activities of mpl ligand analogs that have been assayed using the same assay, using the same conditions including the same internal standard, and having the same analysis of the data used to calculate specific activity, etc.

As used herein the phrases "analog of mpl ligand" or "mpl ligand analog" refer to mpl ligand with one or more changes in the amino acid sequence of mpl ligand which result in a change in the type (N- or O-linked, which may affect the amount of carbohydrate attached), number, or location of sites for carbohydrate attachment. In a preferred embodiment, the change in glycosylation site(s) results in a change in the number of glycosyl chains attached to the mpl ligand molecule. In a particularly preferred embodiment, the change in glycosylation site(s) adds at least one (generally 1-6, preferably 1-5, particularly preferably 2-4) glycosyl chains, and most preferably the chain(s) is(are) added via N-linkage. In another particularly preferred embodiment, the mpl ligand analog retains at least equivalent biological activity in vivo as compared to natural sequence mpl ligand (e.g., human mpl ligand) and may possess substantially higher activity in vivo, as measured in assays for biological activity. Such assays include those that detect megakaryocyte or platelet production.

To prepare such analogs of mpl ligand, preferably they are generated by site-directed mutagenesis resulting in additions, deletions, or substitutions of amino acid residues that add, eliminate or alter sites that are available for glycosylation. By "altered" is meant that a site has been deleted while another has been added at the same or another location as the deleted site. However, as is appreciated by those skilled in the art, other methods could result in a gene encoding the same amino acid sequence, and such methods are encompassed herein. The resulting analogs may have fewer or more (preferably more) attached carbohydrate chains than natural human/recombinant mpl ligand.

Addition of one or more carbohydrate (i.e., glycosyl) chains to mpl ligand is one important object of this invention. Mpl ligand analogs having more carbohydrate chains than those found in the corresponding naturally-occurring amino acid sequence (e.g., 1-332 or 1-174, etc.) are generated by adding glycosylation sites which do not perturb the secondary or tertiary conformation in a way that would substantially reduce biological activity. As used herein the "naturally-occurring" mpl ligand refers to an amino acid sequence having the corresponding number of amino acids as the relevant analog, even if the particular length of mpl ligand species is not actually expressed in the native species. Advantageously, the analog of mpl ligand has up to 6 additional sites for N-glycosylation or O-glycosylation, resulting in the addition of from 1 up to 6 additional N-linked or O-linked carbohydrate chains (or a combination thereof).

For example, a Pro at position 30 is replaced by an Asn and a Val at position 32 is replaced by a Thr to give the sequence Asn-Glu-Thr, which serves as a new site for N-glycosylation (analog N4 below; see Table 1).

Analogs may also be constructed which have two or more additional N-linked chains by combining mutations; for example, analogs N4 and N10 described in Table 1 may be combined to yield an analog with two additional sites for carbohydrate addition (i.e., analog N15 in Table 1). In a like manner analogs with three or more added chains can be constructed. As will be appreciated by those skilled in the art, the subject invention includes many other analogs of mpl ligand having different sites for glycosylation (in terms of number, type or location of site). The mpl ligand analogs of this invention are in all cases particularly preferably based on mpl ligand having a human amino acid sequence (see FIGS. 1 and 2); however, analogs based on mpl ligand sequences from other species (e.g., dog, pig, monkey, mouse or rat) are also contemplated herein.

Insertions of amino acids to create glycosylation sites are also contemplated. For example, a Glu at position 57 is replaced by a Thr and Asn is inserted immediately after Met at position 55 as follows:

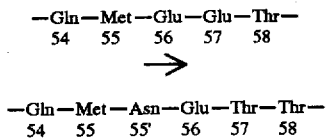

This adds a new glycosylation site (amino acids 55', 56, and 57). See analog N23 below.

Also included within the analogs of this invention are analogs which have one or more amino acids extending from the carboxy terminal end of mpl ligand wherein the carboxy terminal extension provides at least one additional carbohydrate site. The carboxy terminus of mpl ligand will vary depending upon the particular form of mpl ligand used (e.g., mpl ligand 1-332 amino acids, or mpl ligand 1-163 amino acids). An additional carbohydrate site may be added to the carboxy terminus of an mpl ligand species by adding amino acids to the carboxy terminus, such amino acids containing one or more N- or O-linked glycosylation sites.

Tables 1 and 6 list some exemplary mpl ligand analogs which have additional sites for N-linked carbohydrate chains. The analogs have the sequence Asn-X-Ser or Asn-X-Thr included at various positions in the human mpl ligand polypeptide chain based on the human amino acid sequences to create N-linked sites. Tables 4 and 7 list those analogs which add at least one additional N-linked carbohydrate chain, as evidenced by the migration of the glycoproteins on SDS gels (see, Example 6 and FIGS. 3, 5, 6, 7, 9, 10, 12, and 13). Note that these Tables also include some truncated species that are not "analogs" as defined herein (i.e., N1, N16, N17, and N31). These are listed in the Tables to show how various truncated species were prepared.

Also encompassed by the present invention are DNA sequences encoding the mpl ligand analogs disclosed herein, preferably those encoding analogs having additional sites for N-linked chains. Procedures used to introduce changes into the mpl ligand DNA sequence for the purpose of creating, deleting and/or altering attachment sites for carbohydrates are disclosed in Examples 4 and 14.

These mpl ligand analogs can be the product of expression of an exogenous DNA sequence, i.e., produced through recombinant DNA technology, they can be chemically synthesized products or they may be produced by combined methods. An exogenous DNA sequence comprises cDNA, genomic DNA or chemically synthesized DNA encoding an mpl ligand analog. Recombinant DNA plasmids and eukaryotic host cells useful for the expression of such analogs are also provided. Expression vectors include any vector which is capable of expressing cloned DNA sequences in a eukaryotic host cell, particularly those vectors used for expression in COS and CHO cells. Examples of such vectors include plasmids pDSRα and pDSRα2, see *Mol. Cell. Biol.* 8:466–472 (1988); WO 91/13160 (1991); and WO 90/14363 (1990). The cultivation of COS and CHO host cells expressing mpl ligand analogs was carried out using standard procedures known to those skilled in the art.

Changing the number, type, location, or amount of carbohydrate chains attached to mpl ligand may confer advantageous properties such as increased solubility, greater resistance to proteolysis, reduced immunogenicity, increased serum half-life, and increased or altered biological activity.

Conditioned media from COS cells expressing mpl ligand analogs N2–N15 (N1 is human mpl ligand 1-174; see FIG. 2) were analyzed for in vitro biological activity and the results shown in Table 4.

Conditioned media from COS cells expressing mpl ligand analogs/truncations N15-N40 were analyzed for in vitro biological activity and the results are shown in Table 7.

Figure 11:
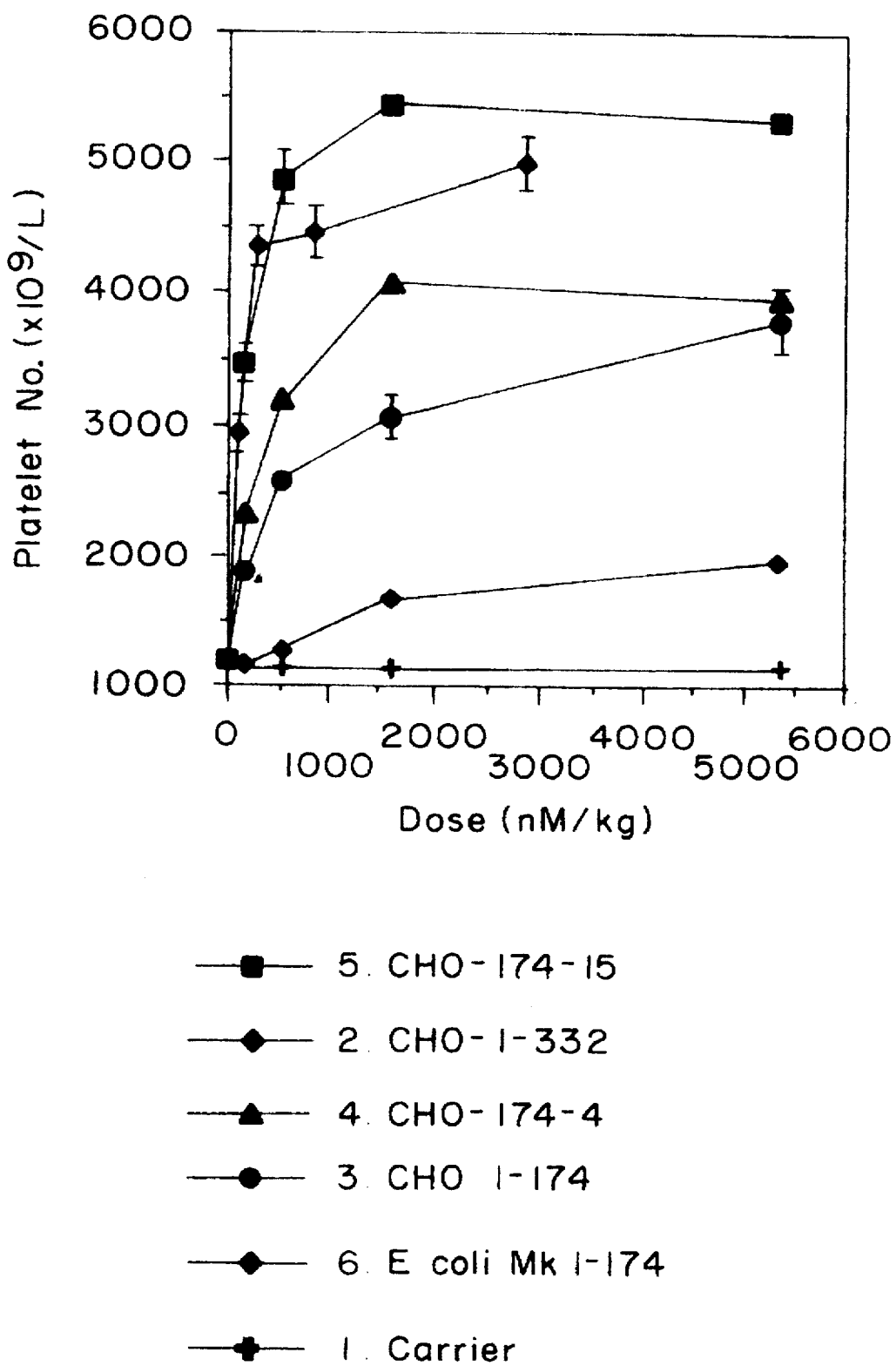
FIG. 11 shows platelet counts from mice treated with various forms of mpl ligand at various doses. The data demonstrate that increased amounts of N- and/or O-linked carbohydrate result in increased in vivo activity.

In vivo biological activity results for various forms are presented in FIG. 11 (see Example 13).

Another embodiment of the invention relates to mammalian (e.g., Chinese Hamster Ovary, CHO) host cells which preferentially synthesize mpl ligand or analogs of mpl ligand having greater than a specific number of sialic acids per molecule, e.g. greater than that found in mpl ligand 1-332, 1-199, 1-191, 1-183, 1-174, 1-163, 1-153, 1-152, or 1-151 produced naturally or recombinantly in a eukaryotic cell. In vitro activities of analogs N4 and N15, along with full-length and various truncated species expressed in CHO cells are shown in Table 5.

The sialic acid content of the mpl ligand molecule may affect its in vivo biological activity. For example, tetraantennary (four-branched) N-linked oligosaccharides most commonly provide four possible sites for sialic acid attachment while bi- and triantennary oligosaccharides, which can substitute for the tetraantennary form at asparagine-linked sites, commonly have at most only two or three sialic acids attached. O-linked oligosaccharides commonly provide two sites for sialic acid attachment. Thus, mpl ligand molecules with N-linked carbohydrate substituted for O-linked carbohydrate can accommodate two additional sialic acids per chain provided the N-linked oligosaccharides are tetraantennary. Mammalian cell cultures are screened for those cells that preferentially add tetraantennary chains to recombinant mpl ligand, thereby maximizing the number of sites for sialic acid attachment.

Dihydrofolate reductase (DHFR) deficient Chinese Hamster Ovary (CHO) cells are a commonly used host cell for the production of recombinant glycoproteins including recombinant mpl ligand.

Compositions comprising a therapeutically effective amount of an mpl ligand analog in accordance with this together with a suitable diluent, adjuvant and/or carrier useful in mpl ligand therapy are further encompassed by this invention. A "therapeutically effective amount" as used herein refers to that amount which provides therapeutic effect for a given condition and administration regimen.

The present compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art. The specific route chosen will depend upon the condition being treated. The administration of mpl ligand or mpl ligand analogs is preferably done as part of a formulation containing a suitable carrier, such as human serum albumin, a suitable diluent, such as a buffered saline solution, and/or a suitable adjuvant. The required dosage will be in amounts sufficient to raise the platelet levels of patients and will vary depending upon the severity of the condition being treated, the method of administration used and the like.

The conditions to be treated by the methods and compositions of the present invention are generally those which involve an existing megakaryocyte/platelet deficiency or an expected megakaryocyte/platelet deficiency in the future (e.g., because of planned surgery). Such conditions will usually be the result of a deficiency (temporary or permanent) of active mpl ligand in vivo. The generic term for platelet deficiency is thrombocytopenia, and hence the methods and compositions of the present invention are generally available for treating thrombocytopenia.

Thrombocytopenia (platelet deficiencies) may be present for various reasons, including chemotherapy, bone marrow transplants, and other therapy with a variety of drugs, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery or future thrombocytopenia-inducing therapy, an mpl ligand analog of the present invention could be administered several days to several hours prior to the need for platelets. With regard to acute situations, e.g., accidental and massive blood loss, an mpl ligand analog could be administered along with blood or purified platelets.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors.

Generally, the daily regimen should be in the range of 0.01–1000 micrograms of mpl ligand analog per kilogram of body weight, preferably 0.1–10 micrograms per kilogram of body weight.

The therapeutic methods, compositions and polypeptides of the present invention may also be employed, alone or in combination with other cytokines, soluble mpl (i.e., mpl ligand) receptor, hematopoietic factors, interleukins, growth factors or antibodies in the treatment of disease states characterized by other symptoms as well as platelet deficiencies. It is anticipated that an mpl ligand analog molecule will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), GM-CSF, granulocyte colony stimulating factor (G-CSF), EPO, interferon-alpha (IFN-alpha), IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of mpl ligand analog (to enhance the number of mature megakaryocytes) followed by administration of the soluble mpl receptor (to inactivate the analog and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

Additional modifications of the analogs of this invention may also be carried out, e.g., to increase activity, stability, half-life, etc. For example, pegylation (poly- or mono-) could be added to the mpl ligand analog via amino groups on the protein or via the carbohydrate groups. Also, fatty acids or other polymers could be attached to the protein or carbohydrate groups.

The following examples are offered to more fully illustrate the invention, but are not to be construed as limiting the scope thereof. The mpl ligand standard used in the bioassays employed in the Examples is a recombinant mpl ligand standard that was expressed in *E. coli*, refolded into an active conformation and purified. Thus, only relative specific activities are being measured.

EXAMPLE 1

Construction of Mpl Ligand 1-174

Human mpl ligand gene encoding amino acids 1-174 (starting with S-P-A-P-P-A . . . ) of FIG. 2 was generated from a human fetal liver cDNA library (Bartley et al, *Cell* 77: 1117–1124 (1994) by polymerase chain reaction (PCR). The 5' PCR primer encoded the amino terminus of human mpl ligand, an XbaI site, and an optimized Kozak sequence. The 3' primer contained a termination codon and a SalI restriction site. The amplified DNA fragment was digested with XbaI and SalI then ligated to XbaI and SalI cut pDSRα2. The resultant plasmid, pDSRα2 mpl ligand 1-174 was used for mammalian cell expression. The sequence of the resulting gene (including the signal peptide) is shown in FIG. 2.

Plasmid DNA containing mpl ligand 1-174 was digested with XbaI and SalI restriction enzymes, the resulting DNA fragments were subjected to agarose gel electrophoresis, and the 605 nt mpl ligand 1-174 DNA fragment was isolated from the gel using a GeneClean™ kit and procedures supplied by the manufacturer (BIO 101, Inc.). Plasmid pDSRα2 as described in WO 90/14363 (1990) was also digested with XbaI and SalI restriction enzymes and the vector fragment was recovered. Ligation of the two fragments results in pDSRα2 (mpl ligand 1-174).

EXAMPLE 2

Expression of Mpl Ligand 1-174 in CHO Cells and Purification

Dihydrofolate reductase deficient (DHFR⁻) Chinese Hamster Ovary (CHO) cells were transfected with pDSRα2-mpl ligand 1-174. A 100 mm tissue culture dish was plated with $1\times10^6$ CHO DHFR⁻ cells grown in CHO D⁻ medium (DMEM, 10% Fetal bovine serum, 1% penicillin/streptomycin/glutamine, 1% nonessential amino acids (Gibco) and 1% HT supplement (Gibco)) the day before transfection. Four transfections were performed. For each transfection, plasmid DNA (50 ug) was linearized by digesting with Pvu I and Buffer H (Boehringer Mannheim). A DNA precipitate was then formed and added to the plates dropwise as per the Mammalian Cell Transfection Kit (Speciality Media). After 24 hours in a tissue culture incubator the medium was replaced with fresh CHO D- medium. Twenty four hours later the cells were split into 96 well tissue culture plates with 100 ul of CHO select medium (D-MEM, 5% dialyzed fetal Bovine serum, 1% penicillin/streptomycin/glutamine, 1% nonessential amino acids (Gibco)) per well and transformants were selected. Medium was changed weekly until colonies appeared. After two weeks, mpl ligand expression was screened for using the 32D cell proliferation assay described below (see Example 9). Those clones expressing in excess of $1\times10^5$ units/ml were expanded and frozen in cryogenic storage. One clone was expanded for roller bottle production and approximately 8 liters of conditioned medium was produced.

Plasmid pDSRα2 containing mpl ligand 1-174 cDNA was transfected into DHFR-deficient CHO cells as explained above. Two liters of serum-free CHO cell conditioned medium (50% D-MEM, 50% HAMS-F12, 1% penicillin/streptomycin/glutamine, 1% nonessential amino acids (Gibco)) from roller bottles seeded with CHO cells expressing mpl ligand 1-174 was concentrated 15 fold using a 2L Amicon Model 2000 stirred cell and a 10,000 dalton molecular weight cut-off membrane (YM10, Amicon). Forty-five milliliters of concentrated conditioned medium was then loaded directly onto a 4 ml hu-MPL-X affinity column at a flow rate of 0.4 ml/min using a Pharmacia FPLC. The affinity column was constructed by coupling 1.5–2.5 milligrams of Mpl-X (the soluble extra-cellular domain of the mpl receptor) per milliliter of Pharmacia CNBr activated Sepharose resin as recommended by the manufacturer. After loading, the column was washed with 16 ml of phosphate buffered saline (PBS; 10 mM Na·PO₄ pH 6.8/150 mM NaCl) and then 24 ml of 10 mM Tris, pH 8.0/1M NaCl. Mpl ligand (1-174) was eluted with 40 ml of 20 mM CAPS (3-[Cyclohexylamino]-1 propanesulfonic acid) pH 10.5/1M NaCl/5 mM CHAPS(3-[(3-Cholamidopropyl) dimethylammonio]-1-propanesulfonate) in 6 ml fractions. The second fraction yielded a single band on a 14% SDS gel. This material was concentrated and buffer exchanged against a saline solution of 0.9% NaCl and was biologically active in vitro and in vivo. Other forms of CHO cell expressed mpl ligand were purified in a similar manner.

EXAMPLE 3

In vivo Biological Activity of Recombinant Human Mpl Ligand

Platelet counts from mice treated with various forms of mpl ligand were measured. CHO-derived mpl ligand 1-332, 1-174, 1-163, and 1-153 were produced and purified by Mpl-receptor affinity chromatography. E. coli-derived Met-Lys-mpl ligand 1-332, Met-Lys-mpl ligand 1-174, Met-Lys-mpl ligand 1-163 and Met-Lys-mpl ligand 1-153 were produced and purified by conventional chromatography.

Figure 4:
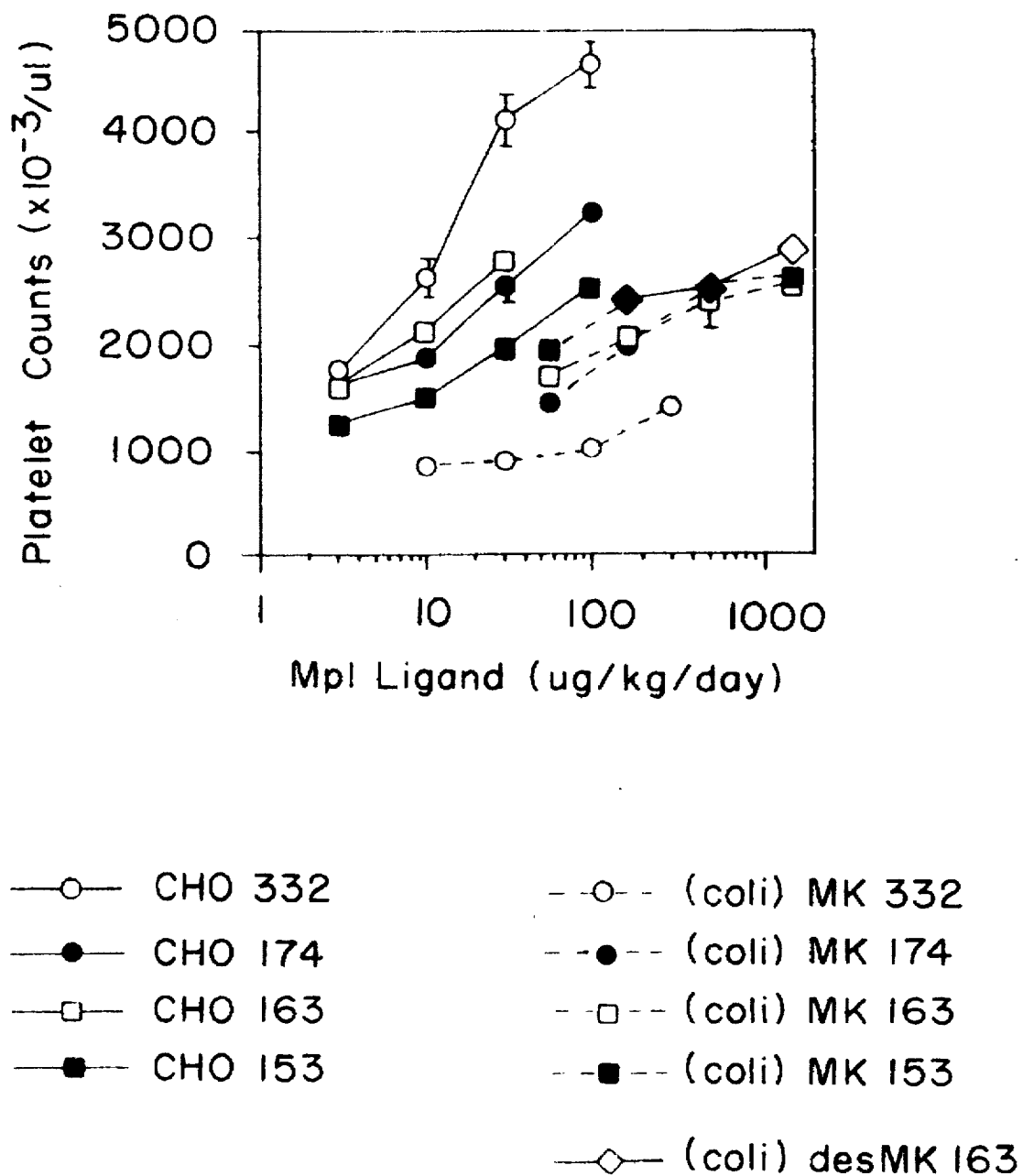
FIG. 4 shows in vivo activity of *E. coli* and CHO expressed mpl ligand in normal mice, in terms of platelet counts. The data indicates that glycosylated mpl ligand (CHO material) has superior activity than non-glycosylated (*E. coli*) material. This may be a result of increased half-life for the glycosylated material. For example, CHO 332 stands for human mpl ligand amino acids 1-332 (FIG. 1) expressed in CHO cells.

FIG. 4 shows platelet counts from mice treated with various forms of CHO cell-derived (solid lines) or E. coli-derived (dashed lines) recombinant human mpl ligand. Normal, female Balb/c mice were injected subcutaneously with the indicated concentration of mpl ligand for 5 consecutive days. Test bleeds from a small lateral cut in a tail vein were collected 24 hours after the last injection. Blood cell analyses were performed with a Sysmex electronic blood cell analyzer (Baxter Diagnostics, Inc. Irvine, Calif.). Data are represented as the mean of determinations of 4 animals, +/− standard error of the mean. Other blood cell parameters such as total white blood cell counts or red blood cell counts were not affected by these treatments (data not shown).

The results indicate that CHO cell expressed forms of mpl ligand have an increased in vivo activity relative to the same forms of mpl ligand produced in E. coli. As described in Example 6, the CHO cell expressed forms of mpl ligand all contain N and/or O-linked carbohydrate and the E. coli expressed mpl ligand forms do not. This indicates that the carbohydrate enhances the in vivo activity of mpl ligand. The increased in vivo activity conferred by the carbohydrate may be a result of increased circulatory half life, increased stability or a combination of both.

EXAMPLE 4

Construction of Mpl Ligand Analogs N2-N15

Procedures for generating additional glycosylation sites for mpl ligand are described below.

The following oligonucleotide primers were synthesized for use in in vitro mutagenesis to prepare analogs N2-N14 (see Table 1 for the structures of these analogs):

| N2- CCCATGTCAATCACAGCAGACT | SEQ ID NO.: 5 |
|---|---|
| N3- CTTCACAGCAACCTGAGCCAGT | SEQ ID NO.: 6 |
| N4- CAGTGCAACGAGACCCACCCTTTG | SEQ ID NO.: 7 |
| N5- GCCTACAAATGTCACGCTGCCTGCT | SEQ ID NO.: 8 |
| N6- CCCACTTGTAACTCATCCCTC | SEQ ID NO.: 9 |
| N7- CAACTGAACGCCACTTGTCTCTCA | SEQ ID NO.: 10 |
| N8- ACTTGTCTCAACTCCACCCTGGGGGA | SEQ ID NO.: 11 |
| N9- CTCCTGGGGAACCTTTCTGGA | SEQ ID NO.: 12 |
| N10- GACCACAAATCACACCGATCCCAAT | SEQ ID NO.: 13 |

-continued

| | | |
|---|---|---|
| N11- | ACCCTTTGTCTACAAATGTCACGCTGCCTGCT | SEQ ID NO.: 14 |
| N12- | TCTCTCAAACCTCACGGGGGAGCTT | SEQ ID NO.: 15 |
| N13- | TGGAAAAATCAGACGGAGGAGAC | SEQ ID NO.: 16 |
| N14- | TGGAGGAGAACAAGACACAGGACAT | SEQ ID NO.: 17 |

To construct m13mp18 mpl ligand 1-174, the gene of FIG. 2 was introduced into XbaI and SalI restriction enzyme digested m13mp18 DNA. Single stranded DNA was recovered from supernatants of *E. coli* strain RZ1032 infected by m13mp18(mpl ligand 1-174) as described by Kunkel et al., *Methods in Enzymol.* 154:367 (1987) and Messing, *Methods in Enzymol.* 101:20 (1983). For in vitro mutagenesis approximately 0.5 µg of single-stranded DNA and 0.125 pmole of one of the synthetic primers described above were mixed with 6 µl of buffer (250 mM Tris pH 7.8, 50 mM MgCl$_2$, 50 mM dithiothreitol and 1% Bovine serum albumin (BSA-Pharmacia)). The primers were previously kinased with ATP and T4 polynucleotide kinase prior to addition. For annealing of the primer to the template, the reaction volume was adjusted to 10 µl with water, the mixture was heated to 65° C. for 5 minutes and then allowed to cool to room temperature. For the elongation reaction 2.5 µl of each of dTTP, dATP, dGTP and dCTP and 1 ml ATP (all at 10 µM) were added, followed by 1 µl (1 unit) of *E. coli* DNA polymerase (Klenow fragment) and 1 µl (1 unit) of T4 DNA ligase. The mixture was then incubated overnight at 14° C. and used to transform *E. coli* JM 109 (Yanisch-Perron et al. *Gene* 33, 103 (1985)) as described (Messing, supra).

To identify mutant clones by differential hybridization, plaques on nutrient agar were transferred to Gene Screen filters (New England Nuclear). The DNA was cross-linked to filters by irradiating them in a UV Stratalinker Model 1800 using the auto cross-link mode (Stratagene). They were then incubated for one hour in 6x SSC(0.9M NaCl/0.09M Na-citrate) containing 1% SDS at 60° C. For the hybridization, the oligonucleotide primer above (8 pmoles) was end-labeled with T4 polynucleotide kinase and $\gamma^{32}$P-labeled ATP and incubated with the filters overnight in 6x SSC, 0.5% SDS and 125 ug/ml herring sperm DNA. The hybridization temperatures were chosen according to estimates of oligonucleotide melting points. Generally the hybridization temperature was approximately 10° C. less than the melting point. The next day, the filters were washed two times with 6X SSC/1% SDS at hybridization temperature followed by two washes with 6x SSC at hybridization temperature and subjected to autoradiography. If necessary, the filters were then washed with 6x SSC at increasing temperatures until little or no hybridization was detected to plaques having the wild-type mpl ligand cDNA sequence. Clones that gave positive hybridization signals under these conditions were identified and retransfected into JM109 to isolate a pure clone. Dideoxy chain termination sequence analysis indicated that the mutations were present.

Double stranded m13 mpl ligand 1-174 DNAs carrying the desired changes were recovered from JM109 transfected cells with QIAGEN kits (Chatsworth Calif.) using methods supplied by the manufacturer. The DNAs were digested with XbaI and SalI and the 605 bp mpl ligand DNA fragments were isolated. pDSRα2 was digested with XbaI and SalI. The vector fragment was isolated and ligated to the mpl ligand fragments above. Recombinant plasmids were identified by restriction analysis. The resulting plasmids (designated mpl ligand 1-174-NX where NX is the analog number) contain DNA encoding mpl ligand analogs having altered amino acid residues at the indicated positions. The resultant plasmids were then sequenced again to confirm the presence of the desired mutations.

The analog N15 was constructed that had two additional N-linked glycosylation sites at positions 30 and 120. PDSRα2 mpl ligand 174-N4 containing Asn30 and Thr32 mutations was digested with XbaI and PstI restriction enzymes and the approximately 385 nt DNA fragment was isolated. PDSRα2 mpl ligand 174-N10 containing Asn120 and Thr122 mutations was digested with PstI and SalI restriction enzymes and the approximately 220 nt DNA fragment was isolated. pDSRα2 was digested with XbaI and SalI. The vector fragment was isolated and ligated to the mpl ligand fragments above. This resulted in PDSRα2 mpl ligand 174-N15 that contains Asn30, Thr32, Asn120 and Thr122 substitutions.

These general procedures were used to construct the mpl ligand analogs shown in Table 1. The DNA sequence changes for each of the analogs are shown; otherwise the oligonucleotide primers used for mutagenesis had sequences complementary to those of human mpl ligand.

TABLE 1

| Analog/ Species No. | Amino Acid Substitution | Sequence Changes |
|---|---|---|
| N1 | (1-174); Pro$^{175}$→Gly$^{332}$ deleted | CCA→TGA (stop codon) |
| N2 | Leu$^{22}$→Asn$^{22}$ | CCT→AAT |
| N3 | Arg$^{25}$→Asn$^{25}$ | AGA→AAC |
| N4 | Pro$^{30}$, Val$^{32}$→Asn$^{30}$, Thr$^{32}$ | CCA,GTT →AAC,ACC |
| N5 | Pro$^{38}$, Leu$^{40}$→Asn$^{38}$, Thr$^{40}$ | CCT,CTG →AAT,ACG |
| N6 | Leu$^{86}$→Asn$^{86}$ | CTC→AAC |
| N7 | Gly$^{82}$, Pro$^{83}$→Asn$^{82}$, Ala$^{83}$ | GGA,CCC→AAC,GCC |
| N8 | Ser$^{87}$, Leu$^{89}$→Asn$^{87}$, Thr$^{89}$ | TCA,CTC→AAC,ACC |
| N9 | Gln$^{92}$→Asn$^{92}$ | CAG→AAC |
| N10 | Ala$^{120}$, Lys$^{122}$→Asn$^{120}$, Thr$^{122}$ | GCT,AAG→AAT,ACC |
| N11 | Pro$^{36}$, Pro$^{38}$, Leu$^{40}$→Ser$^{36}$, Asn$^{38}$, Thr$^{40}$ | CCT,CCT,CTG→TCT,AAT,ACG |
| N12 | Ser$^{88}$Leu$^{90}$→Asn$^{88}$, Thr$^{90}$ | TCC, CTG→AAC,ACG |
| N13 | Thr$^{53}$, Met$^{55}$→Asn$^{53}$, Thr$^{55}$ | ACC,ATG→AAT,ACG |
| N14 | Thr$^{58}$, Ala$^{60}$→Asn$^{58}$, Thr$^{60}$ | ACC,GCA→AAC,ACA |
| N15 | Pro$^{30}$, Val$^{32}$, Ala$^{120}$, Lys$^{122}$→Asn$^{30}$,Thr$^{32}$, Asn$^{120}$, Thr$^{122}$ | CCA,GTT,GCT,AAG→AAC,ACC,AAT,ACC |

Note: Analogs N2-N15 are synonymously referred to herein as analogs 2-15. Further, as used herein, for example, [Asn$^{22}$] mpl ligand means that an asparagine has been substituted for the amino acid at position 22 in the particular mpl ligand species being considered, which is preferably a human sequence having at least amino acids 7-151 of FIG. 1 (including the preferred human mpl ligand sequences set forth herein above). Thus, substitution of an asparagine residue for a leucine residue at position 22 of mpl ligand 1-174 (human sequence) yields an mpl ligand analog that may be represented by [Asn$^{22}$] mpl ligand 1-174.

Plasmids designated pDSRα2 1-174-NX (where NX is the analog number) were constructed by inserting mpl ligand DNA into pDSRα2. The expression vector pDSRα2 is generally described in WO 90/14363(1990). pDSRα2 mpl ligand 1-174-NX plasmids were made by digestion of pDSRα2 with XbaI and SalI. The vector fragment was isolated and ligated to the approximately 605 bp fragments containing the desired sequences.

EXAMPLE 5

Expression of Mpl Ligand and Mpl Ligands N1-N15 in COS Cells cDNA clones of human mpl ligand and mpl ligand analogs described in Table 1 were transferred into COS-1 cells (ATCC No. CRL-1650) by electroporation. COS-1 cells were harvested from semi-confluent dishes, washed with medium (Dulbecco's modified essential medium containing 10% fetal bovine serum and 1% L-glutamine/penicillin/streptomycin (Irvine Scientific)) and resuspended at $6\times10^6$ cells/ml. One half ml of cells was transferred to a 0.2 cm electroporation cuvette (Bio-Rad) and electroporated with a BTX Electroporation System Electrocell Manipulator 600 at 650 uF and 130 volts on the low voltage setting with 50 µg of plasmid DNA encoding the mpl ligand analog. The electroporated cells were plated on 100 mm tissue culture dish in 10 ml of medium. Twelve to twenty four hours after plating the medium was replaced with 10 ml of fresh medium. The conditioned medium was collected 3 to 5 days after electroporation.

EXAMPLE 6

Characterization of Mpl Ligand and Mpl Ligands N1-N15

A. Determination of Carbohydrate Addition

A volume of supernatant containing approximately 30–60 ng mpl ligand or mpl ligand analog from COS cells transfected with mpl ligand analog cDNAs as described in Example 5 was immunoprecipitated overnight at room temperature with a rabbit anti-mpl ligand polyclonal antibody. In some cases where expression was low, a maximum volume of approximately 8–9 ml was used for immunoprecipitation. The antibody was raised to mpl ligand 1-163 that had been expressed and purified from E. coli. Thirty µl of 1:1 Protein A-Sepharose in phosphate buffered saline (PBS) containing 0.1% sodium azide was added to the immunoprecipitate and allowed to incubate for one hour at room temperature. The samples were centrifuged, washed with PBS and resuspended in SDS sample Buffer (0.125M Tris-HCl pH 6.8/4% SDS/20% glycerol/10% β-mercaptoethanol/0.001% bromophenol blue). The samples were analyzed by 12% SDS-polyacrylamide gel electrophoresis, transferred to nitrocellulose and subjected to Western analysis as described (Burnette et al., Anal. Biochem. 112:195–203 (1981); Elliott et al., Gene 79:167–180 (1989)) using a mouse anti-mpl ligand monoclonal antibody raised to a synthetic mpl ligand peptide (e.g., corresponding to amino acid residues 47–62 of FIG. 1). The mpl ligand containing bands were visualized using an ECL kit (Amersham).

Figure 5:
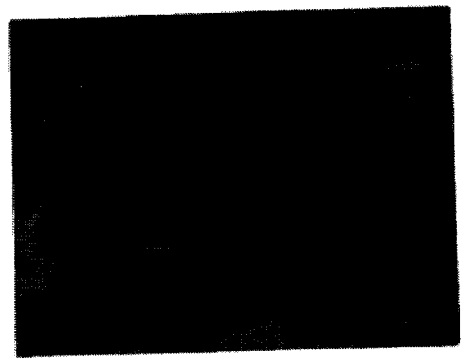
FIG. 5 shows a Western blot analysis of COS cell supernatants of recombinant human mpl ligand and analogs 4, 6, 7, 9, 10, and 11. The construction of the analogs is described in Example 4. Analogs 4, 7, 10 have at least one additional carbohydrate chain as evidenced by slower gel mobility. The analog numbers correspond to analog numbers provided in Table 1 (e.g., 11 corresponds to analog N11). The control is N1 in Table 1.
Figure 6:
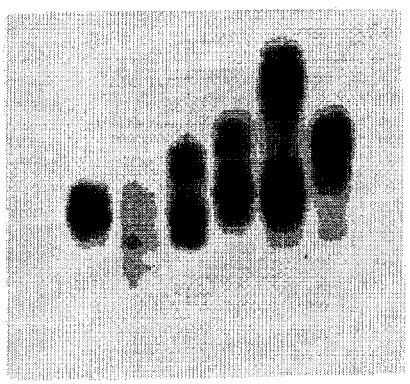
FIG. 6 shows a Western blot analysis of COS cell supernatants of recombinant human mpl ligand and analogs 4, 5, 13, 14, and 15. The construction of the analogs is described in Example 4. Analogs 4, 13, 14, and 15 have at least one additional carbohydrate chain as evidenced by slower gel mobility.

FIG. 5 shows that COS cell supernatants from cells transfected with analogs N4, N7 and N10 DNA revealed increased size compared to human sequence mpl ligand 174 (N1). FIG. 6 shows that COS cell supernatants from cells transfected with N13, N14 and N4 DNA also had increased size compared to human sequence mpl ligand. This increased size is indicative of an additional N-linked carbohydrate chain. N15 contains two additional N-linked glycosylation sites. FIG. 6 indicates that this analog has material with a size greater than analogs containing only 1 additional N-linked glycosylation. The sizes of the proteins were estimated from their mobility on SDS-PAGE relative to protein standards of known molecular weight. The estimated sizes of the larger bands calculated from FIG. 6 are shown in Table 2. This result indicates that N15 contains 2 additional N-linked chains. Western blot analyses of other selected analogs are also shown in FIG. 6.

TABLE 2

N-Linked Carbohydrate Estimates

| Mpl Ligand Analog (1-174) | Molecular Weight (Da) | Molecular Weight Shift(Da) (Over Native) | No. of Potential N-Links Chains (@4 kDa/Site) |
|---|---|---|---|
| N1 (Native) | 23500 | 0 | 0 |
| N4 | 28700 | 5200 | 1 |
| N7 | 27200 | 3700 | 1 |
| N10 | 27200 | 3700 | 1 |
| N13 | 26700 | 3200 | 1 |
| N14 | 28700 | 5200 | 1 |
| N15 | 33500 | 10000 | 2 |

Figure 7:
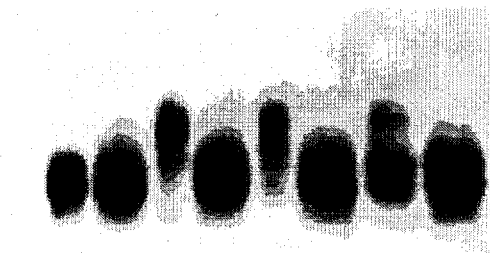
FIG. 7 shows a Western blot analysis of COS cell supernatants of human mpl ligand and indicated mpl ligand analogs after treatment with N-glycanase. The results indicate that the analogs have differential glycosylation patterns.

An experiment was performed to show that the increased size of mpl ligand analogs is due to N-linked carbohydrate. COS cell conditioned medium containing mpl ligand was immunoprecipitated and washed with PBS as described above. To each tube was then added 10 µl 0.5% SDS and each sample was boiled for 3 minutes. Then the following components were added: 10.8 µl of 0.5M NaPO$_4$ pH 8.6, 5 ml of 7.5% nonidet P40 and 3 ul of 250 unit/ml N-glycanase (Genzyme). N-glycanase treatment removes N-linked carbohydrate. Samples were incubated for 6 hours at 37° C. The reaction was stopped by the addition of SDS-PAGE sample buffer and then subjected to SDS-PAGE Western analysis (12% acrylamide) using an anti-mpl ligand monoclonal antibody and an anti-mouse ECL Western Detection Kit (Amersham) as described above. An analysis of N-linked chains using this method is shown in FIG. 7 for human mpl ligand and mpl ligand analogs. Following treatment with N-glycanase the mobility on Western blot for N4, N7 and N10 was reduced to that of N1. As expected, treatment of N1 with N-glycanase had no effect on mobility because N1 has no N-linked glycosylation sites. These results indicate that the increased size observed is due to addition of N-linked carbohydrate.

B. Analysis of O-linked carbohydrate on mpl ligand

To analyze the contribution of O-linked carbohydrate to human mpl ligand, various forms of the protein were purified from CHO cell conditioned media as described above. Each form received +/– treatment with O-glycanase (Glycopeptide alpha-N-acetylgalactos-aminidase, Oxford GlycoSystems). O-glycanase removes O-linked carbohydrate from glycoproteins. The E. coli expressed version of each form was used as an unglycosylated control. To resolve the difference in molecular weight contributed by O-linked carbohydrate, it was necessary to remove any N-linked carbohydrate first. Since the full length version, mpl ligand 1-332, contains N-linked carbohydrate, the CHO cell expressed full length samples received N-glycanase (peptide-N4-(N-acetyl-beta-glucosaminyl) asparagine amidase) treatment as described above for COS cell expressed mpl ligand analogs, except that the N-glycanase treatment was an overnight incubation.

Before proceeding with the O-glycanase treatment on full length (1-332) mpl ligand, the pH range of the sample was adjusted to pH 6.0–pH 7.0 with ¹⁄₁₅ volume of 100 mM acetic acid, pH 2.2. One microgram of protein was denatured by boiling for 3 minutes in SDS and incubated at 37° C. for 60 minutes with 1 U/ml neuraminidase (sialidase, from Arthrobacter urefaciens, Boehringer Mannheim) in 1 mM calcium acetate, pH 6.8 and 20 mM sodium phosphate, pH 6.8.

Subsequent treatment with O-glycanase was done by adding 5 mU of enzyme in a final volume of 100 ul, followed by an overnight incubation at 37° C. Proteins (0.2 ug/lane) were separated by SDS-PAGE (15% acrylamide). Following transfer to 0.2 um nitrocellulose and overnight incubation with anti-mpl ligand polyclonal antibody the mpl ligand proteins were visualized using an anti-rabbit ECL Western Detection Kit (Amersham).

FIG. 3 shows a Western blot of four different forms of human mpl ligand. Full length mpl ligand 1-332 is represented in lanes 1–3, mpl ligand 1-174 lanes 4–6, mpl ligand 1-163 lanes 7–9, and mpl ligand 1-153 lanes 10–12. Treatment with neuraminidase and O-glycanase, shown in lanes 2, 5, 8, and 11, reduced the molecular weight to that of unglycosylated materials, lanes 3, 6, 9, and 12. In every case the mobility increased to that of the unglycosylated version expressed in *E. coli*. These results indicate that the larger sized bands, in lanes 1, 4, 7, and 10 are due to O-linked carbohydrate. The molecular weight of each of the bands was estimated by comparing their mobilities to proteins of known molecular weight.

As seen in Table 3 which shows estimated molecular weights of the different proteins, the apparent shift in mobility could account for as many as 14 O-linked carbohydrate chains (assuming 950 daltons/chain) for mpl ligand 1-332, 9 chains for mpl ligand 1-174, 4 chains for mpl ligand 1-163, and 2 chains for mpl ligand 1-153. The sample run in lane 2 is full length mpl ligand 1-332. It would appear that this protein was degraded, possibly due to extended incubation in glycoenzymes at 37° C. Therefore, the *E. coli* expressed unglycosylated version in lane 3 was used to calculate the approximate molecular weight of O-linked carbohydrate added to CHO cell expressed mpl ligand 1-332.

These results are consistent with the presence of carbohydrate on all the CHO expressed forms of mpl ligand tested. The presence of O-linked carbohydrate was confirmed for CHO cell expressed mpl ligand 1-332, 1-174, and 1-163 by direct analysis of monosaccharide composition. Sialic acids, GalNAc and Gal were released from glycoproteins by acid hydrolysis. The monosaccharides were detected by high pressure anion exchange chromatography and pulsed amperometric detection. All three sugars were detected in each of the forms of mpl ligand. This result is indicative of the presence of sialic acid containing O-linked carbohydrate. This data correlates with the in vivo data as seen in FIG. 4 where CHO cell expressed forms of mpl ligand were all more active in vivo than the equivalent forms expressed in *E. coli*. Thus, the presence of carbohydrate enhances the in vivo activity of mpl ligand.

TABLE 3

O-Linked Carbohydrate Calculations

| Mpl Ligand Form | O-Glycanase Treatment (+/−) | Molecular Weight (Da) | Molecular Weight Shift | # of Potential O-Linked Chains (@950 Da/Chain) |
|---|---|---|---|---|
| 1-332 | − | 54200 | 13600 | 14 |
| 1-332 | *E. coli* version | 40600 | | |
| 1-174 | − | 24600 | 8600 | 9 |
| 1-174 | + | 16000 | | |
| 1-163 | − | 18400 | 3900 | 4 |
| 1-163 | + | 14500 | | |
| 1-153 | − | 15200 | 2300 | 2 |
| 1-153 | + | 12900 | | |

EXAMPLE 7

Mpl Ligand ELISA Assay

Polyclonal antibody production—New Zealand White rabbits were hyperimmunized over a period of three months with recombinant human mpl ligand 1-163 produced in *E. coli*. Antisera from six rabbits exhibiting high antibody titers were pooled and specific anti-mpl ligand antibodies were affinity purified.

Affinity purification—Recombinant human mpl ligand 1-163 was covalently attached to Actigel-ALD (Sterogene Bioseparations, Inc.) according to the manufacturer's instructions. An aliquot of the rabbit antisera pool was added to the mpl ligand affinity gel, and the slurry was agitated gently on a rocker platform overnight a 4°–8° C. Unbound serum proteins were washed from the gel bed with PBS and specifically bound anti-mpl ligand antibodies were then eluted with ImmunoPure Gentle Ag/Ab Elution Buffer (Pierce Chemical Co.) Recovered antibodies were dialyzed against several changes of PBS, then the antibody solution was concentrated in an Amicon stirred cell ultrafiltration unit and the resultant antibody concentrate was the source of specific anti-mpl ligand antibodies subsequently used for well coating and enzyme conjugate preparations.

ELISA reagents—Immulon 4 Removawell Strips (Dynatech Laboratories, Inc.) were coated with affinity purified rabbit anti-mpl ligand antibodies. Affinity purified antibodies were diluted in 0.1M sodium bicarbonate (freshly prepared pH about 8.2) to a concentration of 2.5 ug/ml. Each well received 100 ul of antibody and the plates were incubated for 24 hrs at room temperature in a sealed and humidified chamber. Then, 200 ul of a blocking solution consisting of 1% fetal bovine serum 5% sucrose in TEN (50 mM Tris 7.4/10 mM EDTA/150 mM NaCl) was added to each well and plates were incubated and additional 24 hrs at room temperature in a sealed and humidified chamber. Combined coating and blocking solutions were removed from the wells. An additional overcoating/blocking step was included: 300 ul of SuperBlock Blocking Buffer in PBS (Pierce Chemical Co.) was added to each well. After standing at room temperature for about 5 min, this solution was removed and the wells were allowed to air dry at room temperature for 24 hrs. The coated wells were stored in sealed plastic bags at 4°–8° C. until used in the mpl ligand ELISA.

Affinity purified anti-mpl ligand antibodies from a rabbit antisera pool were covalently coupled to horseradish peroxidase (HRPO) for use as the signal generating antibody. The affinity purified antibodies were derivatized with iminothiolane HCl (Fluka Chemical Corp.). Separately, HRPO was derivatized with N-succinimidyl 6-maleimidocaproate (Fluka Chemical Corp.). The two activated proteins were combined to permit covalent coupling. The reaction mixture was then chromatographed down a FPLC Superose 6 (Pharmacia) column to isolate the antibody:HRPO conjugate of the desired molecular weight (i.e. about 200 kD). Fractions containing the desired conjugate were combined and concentrated in a Centricon 30 (Amicon Division, W. R. Grace & Co.) and stored as a 50% glycerol solution at −20° C. This anti-mpl ligand Ab:HRPO concentrate was diluted into 2% fetal bovine serum in PBS for use in the ELISA. The final concentration of conjugate used in the ELISA was 250–500 ng/ml.

Recombinant human mpl ligand 1-163 produced in *E. coli* cells, was used for the preparation of standards. This mpl ligand was diluted into 2% fetal bovine serum (Sigma Chemical Co.) in TEN buffer containing 0.05% thimerosal as a preservative. Standards prepared contained 1.0, 0.5, 0.25, 0.125 and 0.062 ng/ml mpl ligand.

Assay-100 ul of mpl ligand standards or samples was added to wells then incubated for 18–24 hrs at room temperature in a sealed and humidified chamber. The well contents and residual solution were then removed and the wells washed once with wash solution (0.05% Tween 20 in TEN buffer). Anti-mpl ligand Ab:HRPO conjugate solution (100 ul) was added to each well and then incubated for 2 hrs at room temperature in a sealed and humidified chamber. The contents of wells were removed then washed 4 times with 0.05% Tween 20 in TEN buffer.

For color development, 100 ul of TMB/peroxide substrate solution (Kirkegaard & Perry Solutions A & B mixed 1:1) was added and incubated for 20 min at room temperature. The reaction was stopped by addition of 100 ul stop solution (0.5N sulfuric acid) and the absorbance was read at 450 nm on microtiter plate reader. Concentrations of mpl ligand in samples were calculated from a standard curve generated by using a curve fit program.

EXAMPLE 8

Biological Activity of Mpl Ligand 1-174 Analogs in a Short-Term Liquid Culture Megakaryocyte Assay Analogs of mpl ligand 1-174 were prepared as described above and assayed for their ability to stimulate the growth of megakaryocytes in liquid culture. CD34 selected cells isolated from human leukapheresis units (Nichol et al., *Stem Cells* 12:494–505 (1994)) were plated at $2 \times 10^5$/ml in culture medium (IMDM/1% Pen-Strep Glutamine/1% Nonessential Amino Acids/1% MEM Na-Pyruvate/1% MEM Vitamins/10% deionized BSA/10% normal human AB plasma/10 uM alpha-thiacylglycerol/20 ug/ml L-Asparagine). In addition, 1.5 ul of COS-1 conditioned medium containing mpl ligand (1-174) or mpl ligand 1-174 analog was added to each well. The final volume was 15 ul in Terasaki-style microtiter tissue culture plates (Vangard International). Cells were incubated at 37° C. for eight days in humidified boxes in 5% $CO_2$, fixed directly to the culture wells with 1% glutaraldehyde, and then incubated with a monoclonal antibody cocktail consisting of anti-GPIb, anti-GPIIb, (Biodesign) and anti-GPIb (Dako, Carpinteria, Calif.). The immune reaction was developed with a streptavidin-β-galactosidase detection system (HistoMark, Kirkegaard and Perry). Megakaryocytes, identified by the darker color (blue in actual photographs), appear in FIG. 8.

Panels A and D of FIG. 8 are the positive and negative controls respectively. The well pictured in panel A received 37.5 pg of wild type mpl ligand 1-174 COS-1 conditioned medium and shows substantial megakaryocyte growth. Panel D received 1.5 ul of COS-1 mock conditioned medium and shows no growth. Panels B and C of FIG. 8 are mpl ligand 1-174 analogs N7 and N10 respectively. Panel B received 9.0 pg of mpl ligand COS-1 conditioned medium while panel C received 27 pg and both show excellent megakaryocyte growth.

This experiment indicates that the analogs of mpl ligand tested are capable of stimulating the growth of human megakaryocytes in vitro.

EXAMPLE 9

Biological Activity of Mpl Ligand 1-174 Analogs in an In Vitro Cell Proliferation Assay Analogs of mpl ligand 1-174 were prepared as described above and assayed for their ability to stimulate the proliferation of 32D-mpl cells. To construct 32D-mpl cells, the full length human mpl receptor sequence (Vigon, L. et al., *PNAS* 89:5640–5644 (1992)) was subcloned into an expression vector containing the transcriptional promoter of Moloney Murine Sarcoma virus. Six ug of this construct and 6 ug of an amphotrophic retroviral packaging construct (Landau, N. R., Littman, D. R., *Journal of Virology* 66:5110–5113 (1992)) were transfected into $3 \times 10^6$ 293 cells using a $CaPO_4$ mammalian transfection kit (Stratagene). The same cells were retransfected after 2 days and again after 4 days. The day after the last transfection the 293 cells were cocultivated with the IL-3 dependent murine cell line (32D, clone 23; Greenberger et al., *PNAS* 80:2931–2936 (1983)). After 24 hours, the 32D cells were rescued and banded in a BSA gradient (Path-o-cyte; Miles Inc.). Cells were expanded in 1 ng/ml murine IL-3 and then were selected for growth in 20% APK9 serum (Bartley et al., *Cell* 77:1117–1124 (1994). Cells were sorted for cell surface expression of receptor by FACS using a polyclonal rabbit antipeptide (MPL) serum. These cytokine dependent murine 32D-mpl cells are responsive to mpl ligand. 32D-MPL cells were grown in MEM medium containing 10% Fetal Clone II Serum (Hyclone Laboratories) and 1.0 ng/ml muIL3 to a cell density of $1 \times 10^6$ cells/ml. Cells were collected by centrifugation (approx. 500 XG) and washed twice in growth medium lacking muIL3 and resuspended at $1 \times 10^5$ cells/ml.

An extended twelve point mpl ligand standard curve was prepared using mpl ligand 1-163 and ranges from 5000 to 1 pg/ml. A volume of 100 ul of each dilution of standard mpl ligand or assay sample was added to appropriate wells of a 96 well microtiter tissue culture plate containing 100 ul of resuspended cells (10,000 cells/well) and incubated in a humidified incubator at 37° C. and 10% $CO_2$. After 48 hours, 40 ul of MTS reagent (Aqueous Non-Radioactive Cell Proliferation Kit, Promega) was added to each well and 14–18 hours later the plates were read on a plate reader at 490 nM. The in vitro activity in samples was calculated from a dose response curve for each sample. One unit was defined as the amount of mpl ligand in each sample required to give 50% of maximal stimulation. Specific activity was calculated by dividing the biological activity in units/ml by the mpl ligand concentration in ng/ml as determined by mpl ligand ELISA.

The specific biological activity of mpl ligand analogs transfected and expressed in COS cells is shown in Table 4. The effect of the amino acid substitutions on carbohydrate addition is also summarized. Purified human sequence mpl ligand has an in vitro activity that was 200–300 uniting as determined by the above-mentioned assays. It is apparent from Table 4 that mpl ligand analogs containing additional N-linked carbohydrate are expressed as well as native sequence mpl ligand even when they contain additional carbohydrate chains (as determined in Example 6, Section A) e.g., N4 and N10. Both of these analogs retained full in vitro biological activity also. Therefore the mpl ligand analogs containing N-linked carbohydrate can be expressed normally in mammalian cells and they can have normal or enhanced in vitro biological activity.

TABLE 4

| Mpl Ligand Form (Amino Acid Length) | Sequence | Number of N-linked chains (a) | Elisa (ng/ml) (b) | In Vitro Activity (units/ml) (c) | Specific Activity (units/ml) (d) |
|---|---|---|---|---|---|
| MOCK | NONE | 0 | <0.08 | <10 | <125 |
| N1 (174) | Native | NA | 25 | 5375 | 215 |
| N1 (174) | Native | 0 | 31.4 | 8800 | 280 |
| N1 (174) | Native | 0 | 31.75 | NA | NA |
| N2 (174) | N22 | 0 | NA | NA | NA |
| N3 (174) | N25 | NA | 1.85 | 636 | 344 |
| N4 (174) | N30T32 | 1 | 38 | 8830 | 232 |
| N4 (174) | N30T32 | 1 | 24 | NA | NA |
| N5 (174) | N38T40 | 0 | 1.2 | <10 | <8 |
| N6 (174) | N86 | 0 | 0.44 | <10 | <22 |
| N7 (174) | N82A83 | 0 to 1 | 6 | 2660 | 443 |
| N7 (174) | N82A83 | 0 to 1 | 4.7 | 3080 | 655 |
| N9 (174) | N92 | 0 | 10.5 | 1970 | 188 |
| N10 (174) | N120T122 | 1 | 20.4 | 5943 | 291 |
| N10 (174) | N120T122 | 1 | 33.7 | 9690 | 288 |
| N11 (174) | S36N38T40 | NA | <0.625 | <10 | <16 |
| N11 (174) | S36N38T40 | 0 | 1.3 | <10 | <8 |
| N13 (174) | N53T55 | 0 to 1 | 67 | 18000 | 269 |
| N14 (174) | N58T60 | 0 to 1 | 17.9 | 4850 | 271 |
| N15 (174) | N30T32N120T122 | 0 to 2 | 26 | 6420 | 247 |

NOTES
(a) The number of additional N-linked chains was estimated based upon the mobility of the analog polypeptides in SDS gels as described in Example 6.
(b) Quantities of mpl ligand analogs in CHO cell supernatants were determined by ELISA assay as described in the Examples.
(c) In vitro activity was determined by measuring stimulation of thymidine uptake in 32D cells dependent on mpl ligand for growth.
(d) Ratio of in vitro activity of mpl ligand analog as measured by proliferation assays to amount of mpl ligand analog measured by mpl ligand ELISA.
N.A. Not available.

EXAMPLE 10

Expression in CHO cells and Purification of Mpl Ligand 1-174, N4 and N15 pDSRα2 containing mpl ligand 1-174, N4 and N15 cDNA was transfected into DHFR-deficient CHO cells using the protocol described in Example 2 with the following modifications.

One transfection was performed for each analog. Three weeks after the transfection, mpl ligand expression was screened by mpl ligand ELISA. Three expressing clones for each form were frozen in cryogenic storage. The highest expressing clone for each analog was expanded for roller bottle production. For N4, 7.4 liters of conditioned medium (50% D-MEM, 50% HAMS-F12, 1% penicillin/streptomycin/glutamine, 1% nonessential amino acids (Gibco)) was produced and for N15, 4.6 liters of conditioned medium was produced.

Serum-free CHO cell conditioned medium from roller bottles seeded with CHO cells expressing mpl ligand 1-174 (2.9 L), N4 (7.4 L), N15 (4.4 L) was concentrated 12-, 19-, and 12-fold respectively using a S1Y10 (10,000 dalton molecular weight cut-off) Amicon Spiral ultrafiltration cartridge. One hundred fifty milliliters of concentrated conditioned medium was then loaded directly onto a 3.3 ml hu-MPL-X (receptor) affinity column at a flow rate of 0.3 ml/min. The affinity column was constructed by coupling 1.0–1.5 milligrams of Mpl-X (the soluble extra-cellular domain of the Mpl receptor) per milliliter of Pharmacia CNBr activated Sepharose resin as recommended by the manufacturer. After loading, the column was washed with 30 ml of phosphate buffered saline (PBS; 10 mM NaPO4 pH 6.8/150 mM NaCl) and then 60 ml of 10 mM Tris, pH 8.0/1M NaCl/1 mM CHAPS. Mpl ligand 1-174 was eluted with 30 ml of 20 mM CAPS (3-[Cyclohexylamino]-1 propanesulfonic acid) pH 10.5/1M NaCl/1 mM CHAPS(3-[(3-Cholamidopropyl) dimethylammonio]-1-propanesulfonate).

Fractions were neutralized by adding 0.6 mL 1M Tris pH 7.0 to each eluted fraction. SDS-PAGE analysis showed an apparent "bleeding" of 1-174 mpl ligand during the 10 mM Tris, pH 8.0/1M NaCl 1 mM CHAPS wash. Elution fractions were analyzed by SDS-PAGE. Those fractions containing mpl ligand 1-174 were pooled. This affinity purification was then modified and repeated with the following changes: 0.5 mL/min load and elution, and the removal of the 10 mM Tris, pH 8.0/1M NaCl/1 mM CHAPS wash.

All fractions containing the single mpl ligand band were concentrated using a YM10 (10,000 dalton molecular weight cut-off) membrane in a 50 mL stirred cell, switching to a centricon device. This 0.5 mL concentrate was loaded directly onto a PBS equilibrated Pharmacia Superdex 200 HR 10/30 gel filtration column at 0.25 mL/min collecting 0.25 mL fractions. All eluted fractions containing a single mpl ligand band (based on SDS-PAGE analysis) were pooled.

Other forms (N4 and N15) of CHO cell expressed mpl ligand were purified in a similar manner (two affinity purifications pooled and run on one Superdex 200 gel filtration column).

EXAMPLE 11

Determination of Carbohydrate Addition for CHO Cell Expressed N4 and N15

In order to determine whether N-linked carbohydrate was contained in the mpl ligand forms expressed in CHO cells, conditioned medium was analyzed by SDS-PAGE Western blot as described in Example 6 with the following modifications.

Figure 9:
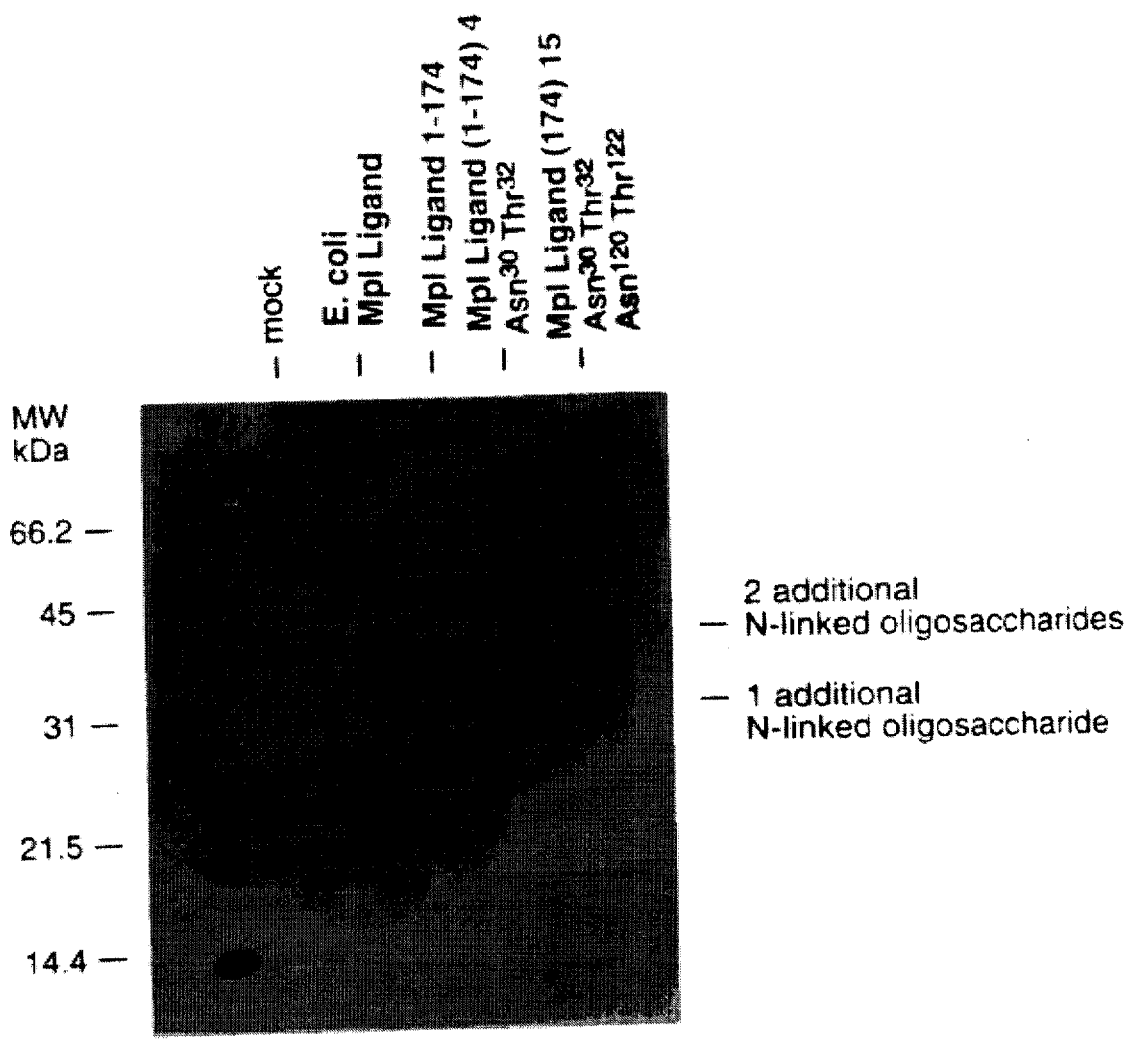
FIG. 9 shows a Western blot analysis of CHO mpl ligand 1-174 and analogs N4 and N15 (see Table 1). Slower gel mobility demonstrates that analog N4 (4B) has one additional oligosaccharide while analog N15 (15-8) has two additional oligosaccharides.
Figure 10:
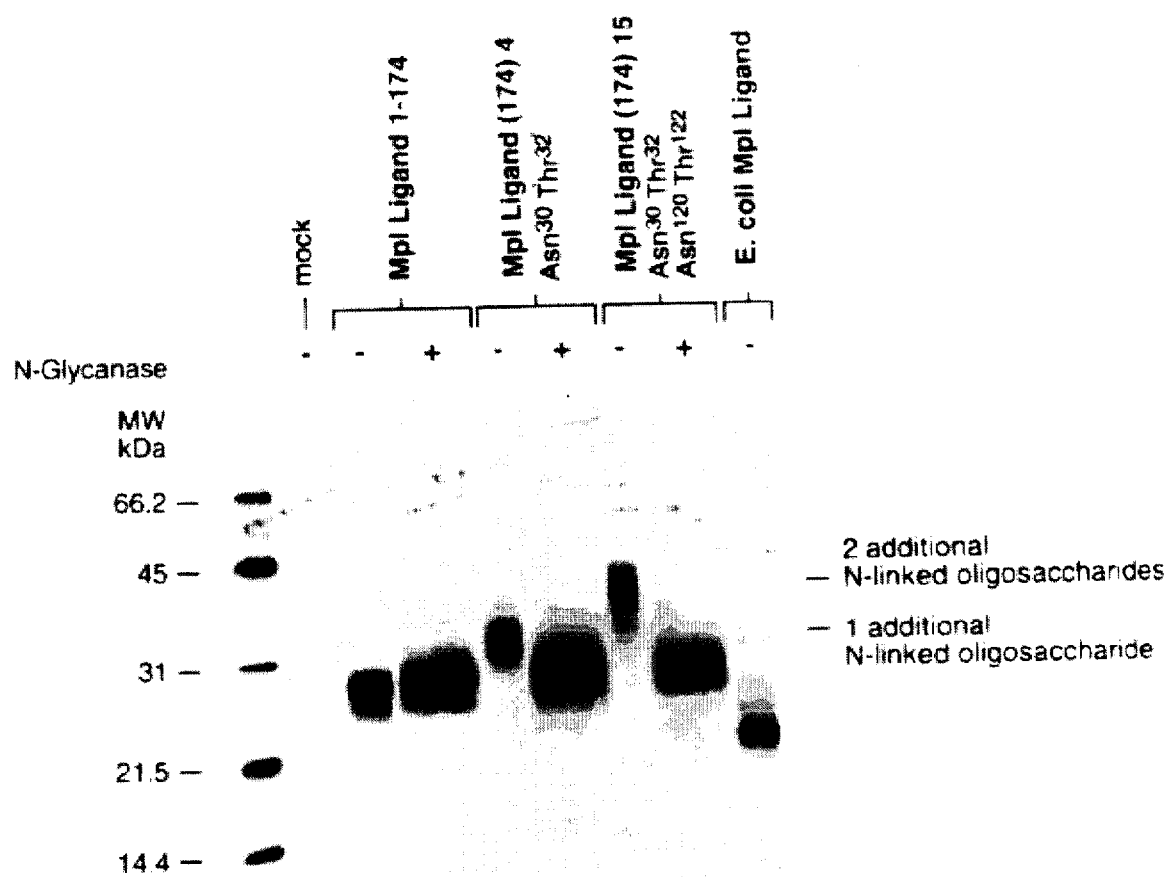
FIG. 10 shows a Western blot of CHO cell-produced mpl ligand analogs with and without treatment with N-glycanase as indicated. Slower gel mobility after treatment with N-glycanase demonstrates the presence of N-linked oligosaccharide.

CHO D-Conditioned medium from roller bottles was used. Samples were loaded into the Centricon-10 centrifugal concentrators (Amicon, Beverly, Mass.) and were spun at 6000 RPM for one hour in a Beckman J2-HS centrifuge using a fixed angle rotor (JA 20.1). A volume of concentrated sample containing approximately 100 ng of the mpl ligand analog was loaded on a SDS PAGE gel together with SDS sample buffer (described in Example 6.) E. coli expressed mpl ligand MK 1-174 containing no carbohydrate was also loaded. FIG. 9 shows differences in mobility that correlate with the expected amount of carbohydrate. The fastest mobility species, Met-Lys (1-174) E. coli mpl ligand, was followed by mpl ligand 1-174 (CHO), N4 (CHO), and N15 (CHO) in succession. See FIG. 9. The most likely explanation for size increases relative to unglycosylated mpl ligand is additional O-linked carbohydrate on mpl ligand 1-174 (CHO), additional O-linked carbohydrate and one additional N-linked oligosaccharide on N4 (CHO), and additional O-linked carbohydrate and two additional N-linked oligosaccharides on N15 (CHO).

In order to establish that the increase in molecular weight was indeed due to the addition of N-linked carbohydrate chains, the samples were treated with N-glycanase to remove any N-linked carbohydrate as described in Example 6. Each sample contained approximately 100 ng of mpl ligand analog purified from conditioned medium.

Following treatment with N-glycanase the mobility of N4 (CHO) and of N15 (CHO) was reduced to that of mpl ligand 1-174 (CHO). Treatment of mpl ligand MK 1-174 (E. coli) or mpl ligand 1-174 (CHO) with N-glycanase did not affect mobility since neither form was expected to contain any N-linked carbohydrate. Comparison of N-glycanase treatment versus no treatment shows that the size difference for N4 corresponds to the size of one N-linked carbohydrate chain and the size difference for N15 corresponds to the size of two carbohydrate chains. Thus addition of N-linked glycosylation sites for these two mpl ligand forms resulted in additional N-linked carbohydrate when these species were expressed in CHO cells. See FIG. 10.

EXAMPLE 12

In vitro Biological Activity of Mpl Ligand Analogs made in CHO cells

Purified mpl ligand and analogs expressed and purified from in CHO cells or E. coli cells were analyzed for in vitro biological activity using the factor dependent cell line 32D-MPL and assay described in Example 9 except activity was calculated from a curve using mpl ligand 1-332 produced in CHO cells as standard. The specific in vitro biological activities of the various forms are shown in Table 5. It is apparent from this Table that the mpl ligand analogs containing additional carbohydrate, which are expressed in CHO cells have in vitro biological activity.

TABLE 5

IN VITRO ACTIVITY OF MPL LIGANDS

| MPL LIGAND FORM | IN VITRO No. N-Linked Chains | ACTIVITY U/mg × 10E6 |
|---|---|---|
| MK174(E. coli) | 0 | 13 |
| 1–163 (CHO) | 0 | 86 |
| 1–174 (CHO) | 0 | 85 |
| N4(CHO) | 1 | 60 |
| N15(CHO) | 2 | 92 |
| 1–332(CHO) | 6 | 41 |

EXAMPLE 13

In vivo Biological Activity of Mpl Ligand Analogs

Platelet counts from mice treated with various forms of mpl ligand were measured and the results are presented in FIG. 11. CHO-derived mpl ligand 1-332, 1-174, N4, and N15 were produced and purified by mpl-receptor affinity chromatography. E. coli-derived Met-Lys-mpl ligand 1-174, was produced and purified by conventional chromatography. The indicated concentration of each form was administered subcutaneously into normal, female Balb/c mice once daily for 5 days. Test bleeds from a small lateral cut in a tail vein were collected 24 hours after the last injection. Blood cell analyses were performed with a Sysmex electronic blood cell analyzer (Baxter Diagnostics, Inc. Irvine, Calif.). Data are represented as the mean of determinations of 4 animals, +/– standard error of the mean. Other blood cell parameters such as total white blood cell counts or red blood cell counts were not affected by these treatments (data not shown).

All the forms stimulated increases in platelet counts. However the activities of the different forms varied. The relative in vivo activity was mpl ligand MK 1-174 (E. coli)<mpl ligand 1-174 (CHO)<N4 (CHO)<mpl ligand 1-332 (CHO)<N15 (CHO). The results indicate that addition of non-naturally occurring N-linked carbohydrate results in increased in vivo activity. It indicates further that increases in the amount of carbohydrate result in proportional increases in in vivo activity.

EXAMPLE 14

Construction of Mpl Ligand Analogs and Truncations N16-N40 by Overlap PCR

Analogs N16 to N40 (see Table 6 for the structures of these analogs) were constructed by overlap PCR (polymerase chain reaction) using a protocol adapted from Cheng et al., PNAS 91, 5695 (1994). Typically one to two mutations were introduced in each construction.

The following oligonucleotide primers were synthesized for use to prepare analogs N16–N40:

| | |
|---|---|
| 5' F CCCTCTAGACCACCATGGAACTGACTGAATTGCTCCTC | SEQ ID NO.: 18 |
| 3' R (1–174) CCCGTCGACTCAGAGCTCGTTCAGTGTG | SEQ ID NO.: 19 |
| N16 - 3' R CCCGTCGACTCACTCCAACAATCCAGAAG | SEQ ID NO.: 20 |
| N17 - 3' R CCCGTCGACTTATCTGGCTGAGGCAGTGA | SEQ ID NO.: 21 |
| N18 - F CACGTCCTTAACAGCAGCCTGAGCCAGTG | SEQ ID NO.: 22 |
| N18 - R CACTGGCTCAGGCTGCTGTTAAGGACGTG | SEQ ID NO.: 23 |

-continued

| | |
|---|---|
| N19 - F CCCTTTGCCTAACGGTTCCCTGCTGCCTGCTGT | SEQ ID NO.: 24 |
| N19 - R ACAGCAGGCAGCAGGGAACCGTTAGGCAAAGGG | SEQ ID NO.: 25 |
| | |
| N20 - F TGCCTACACCTAACCTGTCGCCTGCTGTGGA | SEQ ID NO.: 26 |
| N20 - R TCCACAGCAGGCGACAGGTTAGGTGTAGGCA | SEQ ID NO.: 27 |
| | |
| N21 - F GGAAAACCAATATGTCGGAGACCAAGGCACA | SEQ ID NO.: 28 |
| N21 - R TGTGCCTTGGTCTCCGACATATTGGTTTTCC | SEQ ID NO.: 29 |
| | |
| N22 - F TGGGAGAATGGAACACCACGATGGAGGAGACC | SEQ ID NO.: 30 |
| N22 - R GGTCTCCTCCATCGTGGTGTTCCATTCTCCCA | SEQ ID NO.: 31 |
| | |
| N23 - F AAAACCCAGATGAACGAGACGACCAAGGCACA | SEQ ID NO.: 32 |
| N23 - R TGTGCCTTGGTCGTCTCGTTCATCTGGGTTTT | SEQ ID NO.: 33 |
| | |
| N24 - F CCCAGATGGAGAACACCTCGGCACAGGACAT | SEQ ID NO.: 34 |
| N24 - R ATGTCCTGTGCCGAGGTGTTCTCCATCTGGG | SEQ ID NO.: 35 |
| | |
| N25 - F CACGGGGACAAAACGGAACCACTTGCCTCTCA | SEQ ID NO.: 36 |
| N25 - R TGAGAGGCAAGTGGTTCCGTTTTGTCCCCGTG | SEQ ID NO.: 37 |
| | |
| N26 - F CAGGGCAGGAACACATCTCACAAGGATCCCA | SEQ ID NO.: 38 |
| N26 - R TGGGATCCTTGTGAGATGTGTTCCTGCCCTG | SEQ ID NO.: 39 |
| | |
| N27 - F GGGCAGGACCAACGCTAGCAAGGATCCCAAT | SEQ ID NO.: 40 |
| N27 - R ATTGGGATCCTTGCTAGCGTTGGTCCTGCCC | SEQ ID NO.: 41 |
| | |
| N29 - F pair1 CAGTGCAACGAGTCCCACCCTTGG | SEQ ID NO.: 42 |
| N29 - R pair1 CAAAGGGTGGGACTCGTTGCACTG | SEQ ID NO.: 43 |
| | |
| N29 - F pair2 GACCACAAATCACTCCGATCCCAA | SEQ ID NO.: 44 |
| N29 - R pair2 TTGGGATCGGAGTGATTTGTGGTC | SEQ ID NO.: 45 |
| | |
| N30 - F GTCCCCACCAACACCTCTCTAGTCCTC | SEQ ID NO.: 46 |
| N30 - R GAGGACTAGAGAGGTGTTGGTGGGGAC | SEQ ID NO.: 47 |
| | |
| N31 - 3' R CCCGTCGACTCACTTCAGAAGCCCAGAGCCAGT | SEQ ID NO.: 48 |
| | |
| N36(1) - F GAAAACCCAGAACGAGACCACCAAGGCACAG | SEQ ID NO.: 49 |
| N36(1) - R CTGTGCCTTGGTGGTCTCGTTCTGGGTTTTC | SEQ ID NO.: 50 |
| | |
| N36(2) - F CACCAAGGCACAGGACATTCTGGGAG | SEQ ID NO.: 51 |
| N36(2) - R CTCCCAGAATGTCCTGTGCCTTGGTG | SEQ ID NO.: 52 |
| | |
| N37 - F GAAAACCCAGATGAACGAGACCAAGGCACAG | SEQ ID NO.: 53 |
| N37 - R CTGTGCCTTGGTCTCGTTCATCTGGGTTTTC | SEQ ID NO.: 54 |
| | |
| N38 - F GTCCCCACCAACACCACTCTAGTCCTC | SEQ ID NO.: 55 |
| N38 - R GAGGACTAGAGTGGTGTTGGTGGGGAC | SEQ ID NO.: 56 |

F = Forward

R = Reverse

Constructions that introduce one new glycosylation site were performed in two successive steps. In step 1, two reactions were performed using 4 different oligonucleotides. These oligos included a 5' forward primer, a reverse mutagenic primer, a forward mutagenic primer(usually complementary to the reverse mutagenic primer) and a reverse 3' primer. The reverse 3' primer contained sequences that introduced stop codons followed by SalI restriction sites. Stop codons were introduced at positions 175, 184, 192, and 200. Thus, forms of lengths 1-174, 1-183 (N16), 1-191 (N17), and 1-199 (N31) could be made. PCR1 used template DNA (pDSRα2 containing mpl ligand 1-174 sequences or full length mpl ligand 1-332 sequences), the 5' forward primer and the reverse mutagenic primer. PCR2 used template DNA, the 3' reverse primer and the forward mutagenic primer. The two PCR reactions were then performed and the amplified DNA fragments were separated by agarose gel electrophoresis. Small pieces of agarose containing DNA fragments of the correct size were excised from the gel.

The DNA fragments from PCR1 and PCR2 were combined together and a third PCR reaction was performed using only the 5' forward and 3' reverse primers. Thus, a full length DNA segment containing the desired mutations inserted into mpl ligand was amplified.

The amplified fragments were again separated by agarose gel electrophoresis, the correct sized DNA fragment was purified using a Geneclean™ kit and procedures supplied by the manufacturer (Bio 101, Inc.). The purified DNA was digested with XbaI and SalI, then it was purified again using the Geneclean™ kit. The fragment was then ligated into XbaI and SalI cut pDSRα2. Ligated DNA was precipitated with 2 volumes of ethanol in 0.3M NaOAc pH 5.2 in the presence of carrier tRNA and transformed into E. coli. Clones were tested by restriction analysis and agarose gel electrophoresis to identify those containing the correctly sized DNA inserts. Purified plasmid DNA was then prepared and the mpl ligand insert was sequenced to confirm the presence of the desired mutations and to ensure that no additional amino acid changes were introduced.

In several cases, two or more mutations were combined simultaneously, i.e., see N29, N33, N34, N35, N39 and N40. This could be done by introducing a new substitution into DNA already containing a change. For example, N33 was made by introducing the N23 changes into N15. In this case the procedure above was performed by using N23 mutagenic primers and the N15 template DNA.

In another strategy, two changes could be introduced simultaneously into template DNA. The template DNA could contain natural sequences or could contain sequences encoding mpl ligand forms already containing changes. In these cases step 1 involved 3 PCR reactions and 6 oligos. The oligos included a 5' forward primer, 2 pairs of forward and reverse mutagenic primers, and a reverse 3' primer. Each pair of primers was complementary to each other and contained sequences designed to introduce one new glycosylation site.

PCR1 included template DNA, the 5' forward primer and the reverse mutagenic primer from pair 1. PCR2 included template DNA, the forward mutagenic primer from pair 1 and the reverse mutagenic primer from pair 2 where pair 2 primers are 3' to pair 1 primers. PCR3 included template DNA, the forward mutagenic primer from pair 2 and the reverse 3' primer.

DNA fragments from each PCR reaction were separated by agarose gel electrophoresis and excised as before. The 3 DNA fragments were then combined together and amplified by PCR again using only the 5' forward and 3' reverse primers.

The DNA segment encoding the entire gene of interest with sequences containing two new glycosylation sites was then purified, cut with XbaI and SalI, and ligated into XbaI and SalI cut pDSRα2 as before.

Multiple mutations could also be combined by performing the PCR reactions on templates already containing mutations. For example, N39 was made by introducing N36 and N38 changes into N15 template DNA. This was done using a different set of primers (N36(2)) than that used to make N36 (N36(1)). See primers set forth above. Both sets of primers introduced the same mutation.

Longer mpl ligand forms could also be made. Thus, N40 was made in a similar manner to N39 except the 3' reverse primer in PCR 3, (step 1) and the PCR primer in step 2 was the primer used to make N31. This primer introduces a stop codon at position 200 followed by a SalI restriction site. In addition, the template DNA used for PCR 3 contained sequences encoding full length mpl ligand (1-332).

The typical PCR reaction mix contained: 4 ul each of forward and reverse primers (5 pm/ul), 1 ul template (50 ng), 10 ul of 5X LP buffer (100 mM Tricine pH 8.7/25% glycerol/425 mM KOAc), 10 ul DNTP stock (1 mM each of dATP, dTTP, dCTP, dGTP), 0.8 ul rTh polymerase (Perkin Elmer; 2.5 U/ul), and 2 ul Vent polymerase (NEB; 0.01 U/ul after 1:100 fresh dilution in 1X LP buffer). $H_2O$ was added to bring the final volume to 50 ul. All the components were added together in the order shown and the PCR was started when the temperature during the first cycle was above the 60° C. by adding 1 ul of 50 mM MgOAc. Reaction conditions were: 2 cycles of 94° C., 10 sec/45° C., 1 min/ 68° C., 5 min followed by 25 cycles of 94° C., 10 sec/55° C., 1 min/ 68° C., 5 min.

These general procedures were used to construct the mpl ligand analogs and truncations N16 to N40 shown in Table 6. The DNA sequence changes for each of the forms are shown.

TABLE 6

MPL LIGAND ANALOGS HAVING SITES FOR N-LINKED CARBOHYDRATE CHAINS

| Analog/ Species No. | Amino Acid Substitution | Sequence Changes |
|---|---|---|
| N16 | (1-183); Thr$^{184}$→Gly$^{332}$ deleted | ACA→TGA (stop codon) |
| N17 | (1-191); Thr$^{192}$→Gly$^{332}$ deleted | ACT→TAA (stop codon) |
| N18 | His$^{23}$,Arg$^{25}$→Asn$^{23}$,Sel$^{25}$ | CAC,AGA→AAC,AGC |
| N19 | Thr$^{37}$,Pro$^{38}$,Val$^{39}$→ Asn$^{37}$,Gly$^{38}$,Ser$^{39}$ | ACA,CCT,GTC →AAC,GGT,TCC |
| N20 | Val$^{39}$,Leu$^{41}$→Asn$^{39}$,Ser$^{41}$ | GTC,CTG→AAC,TCG |
| N21 | Gln$^{54}$,Glu$^{56}$→Asn$^{54}$,Ser$^{56}$ | CAG,GAG→AAT, TCG |
| N22 | Lys$^{52}$,Gln$^{54}$→Asn$^{52}$,Thr$^{54}$ | AAA,CAG→AAC,ACG |
| N23 | Glu$^{57}$→Asn$^{55'(i)}$,Thr$^{57}$ | GAG→AAC(i),ACG |
| N24 | Glu$^{57}$,Lys$^{59}$→Asn$^{57}$,Ser$^{59}$ | GAG,AAG→AAC,TCG |
| N25 | Leu$^{81}$,Pro$^{83}$→Asn$^{81}$,Thr$^{83}$ | CTG,CCC→AAC,ACC |
| N26 | Thr$^{118}$,Ala$^{120}$→Asn$^{118}$,Ser$^{120}$ | ACC,GCT→AAC,TCT |
| N27 | Thr$^{119}$,His$^{121}$→Asn$^{119}$,Ser$^{121}$ | ACA,CAC→AAC,AGC |
| N29 | Pro$^{30}$,Val$^{32}$,Ala$^{120}$,Lys$^{122}$→ Asn$^{30}$,Ser$^{32}$,Asn$^{120}$,Ser$^{122}$ | CCA,GTT,GCT,AAG→ AAC,TCC,AAT,TCC |
| N30 | Ser$^{163}$,Arg$^{164}$→Thr$^{163}$,Asn$^{164}$ | AGC, AGA→ACC, AAC |
| N31 | (1-199); Trp$^{200}$→Gly$^{332}$ deleted | TGG→TGA (stop codon) |
| N33 | Pro$^{30,Val32}$,Glu$^{57}$,Ala$^{120}$,Lys$^{122}$ → Asn$^{30}$,Thr$^{32}$,Asn$^{55'(i)}$,Thr$^{57}$ Asn$^{120}$,Thr$^{122}$ | CCA,GTT,GAG,GCT,AAG → AAC,TCC,AAC(i),ACG, AAT, TCC |
| N34 | Pro$^{30}$,Val$^{32}$,Glu$^{57}$Ser$^{163}$,Arg$^{164}$ → Asn$^{30}$,Thr$^{32}$,Asn$^{55'(i)}$,Thr$^{57}$, Thr$^{163}$,Asn$^{164}$ | CCA,GTT,GAG,AGC,AGA → AAC,TCC,AAC(i),ACG, ACC,AAC |
| N35 | N4 + N23 + N30 + N31 (1-199) | — |
| N36 | Met$^{55}$,Glu$^{57}$→Asn$^{55}$,Thr$^{57}$ | ATG,GAG→AAC,ACC |
| N37 | Glu$^{56}$→Asn$^{56}$ | GAG→AAC |
| N38 | Ser$^{163}$,Arg$^{164}$,Ser$^{166}$ →Thr$^{163}$,Asn$^{164}$,Thr$^{166}$ | AGC,AGA,TCT →ACC,AAC,ACT |
| N39 | N4 + N10 + N36 + N38 (1-174) | — |
| N40 | N4 + N10 + N36 + N38 + N31 (1-199) | — |

The symbol "(i)" in the above Table means that the referenced amino acid has been inserted. For example, $Glu^{57} \rightarrow Asn^{55(i)}, Thr^{57}$ (analog N23 in Table 6) means that the Glu at position 57 has been replaced with a Thr and, additionally, an Asn has been inserted just after the Met at position 55, and the Asn has been numbered 55' so that subsequent amino acids retain their previously assigned numbers.

Examples that include all changes from previous Examples are indicated by the specific analog numbers joined by "+" signs. See analogs N35, N39, and N40. The lengths of the amino acid chains of these analogs are indicated parenthetically. Thus, analog N35 contains a combination of all changes made for analogs N4, N23, N30 and N31. The changes indicated for N31 mean that analog N35 is 199 amino acids long. All analogs in Table 6 are 174 amino acids long, except where indicated to be a different length (or, in the cases where an amino acid has been inserted, the total length will be increased by the number of inserted amino acids).

EXAMPLE 15

Characterization of Mpl Ligand Analogs and Truncations N16 to N40

A. Determination of expression level and in vitro biological activity of mpl ligand analogs.

Species N16 to N40 were transfected into COS cells using either the electroporation method (Example 5) or the CaPO4 method (Mammalian cell Transfection Kit; Specialty media). Cell free conditioned medium was collected after 3–4 days, aliquoted and stored at −70° C. Expression level was determined by ELISA assay as described in Example 7. The supernatants were also assayed for biological activity as described in Example 9 with one modification. The activities were calculated from a standard curve using purified CHO cell expressed mpl ligand 1-332 as standard.

The results are shown in Table 7. As shown in Table 7 most of the mpl ligand analogs were expressed and secreted. Some of the analogs appeared to have increased secretion. Bioassays on these samples indicated that the specific activities for most were also comparable to unmodified forms. Some of the analogs contained multiple N-linked carbohydrate chains(see below). This indicates that carbohydrate addition can result in increased secretion and normal in vitro activity of the analogs.

TABLE 7

| Mpl Ligand Form (Amino Acid Length) | Sequence | Number of N-linked chains (a) | Elisa (ng/ml) (b) | In Vitro Activity (units/ml) (c) | Specific Activity (units/ng) (d) |
|---|---|---|---|---|---|
| N1 (174) | Native | 0 | 28 | 3991 | 143 |
| N15 (174) | N30T32N120T122 | 0–2 | 45 | 7003 | 156 |
| N16 (183) | 1-183 | 0 | 85 | 9276 | NA |
| N17 (191) | 1-191 | NA | >0.3 | 11 | NA |
| N18 (174) | N23S25 | 0 | 2 | 5 | 2.5 |
| N19 (174) | N37G38S39 | NA | >0.3 | NA | NA |
| N20 (174) | N39S41 | NA | >0.3 | >10 | NA |
| N21 (174) | N54S56 | 0–1 | 30 | 4380 | 146 |
| N22 (174) | N52T54 | 0–1 | 2 | 856 | 428 |
| N23 (174) | N55'(i)T57 | 1 | 11 | 1059 | 96 |
| N24 (174) | N57S59 | 0 | 5.3 | 458 | 86 |
| N25 (174) | N81T83 | NA | 0.22 | 123 | 559 |
| N26 (174) | N118S120 | NA | 0.9 | 96 | 106 |
| N27 (174) | N119S121 | 0 | 4.5 | 338 | 75 |
| N29 (174) | N30S32N120S122 | 0–2 | 15 | 1627 | 108 |
| N30 (174) | T163N164 | 0–1 | 128 | 15592 | 122 |
| N31 (199) | 1-199 | at least 1 | 156 | 19000 | 122 |
| N33 (174) | 4 + 10 + 23 | 3 | 78 | 10057 | 129 |
| N34 (174) | 4 + 23 + 30 | at least 2 | 112 | 13536 | 120 |
| N35 (199) | 34 + 31 | 4 or more | 172 | 13112 | 76 |
| N36 (174) | N55T57 | 0–1 | 48 | 5808 | 121 |
| N37 (174) | N56 | 1 | 32 | 4504 | 141 |
| N38 (174) | T163N164T166 | 0–1 | 25 | 3904 | 156 |
| N39 (174) | N4 + N10 + N36 + N38 | 3 to 4 | 127 | 17661 | 139 |
| N40 (199) | N4 + N10 + N36 + N38 + N31 | at least 5 | 134 | 19735 | 147 |

NOTES
(a) The number of additional N-linked chains was estimated according to the mobility of the analog polypeptides in SDS gels.
(b) Quantities of mpl ligand analogs in COS cell supernatants were determined by EIA.
(c) In vitro activity was determined by measuring proliferation of 32D-MPL cells which are dependent on mpl ligand for growth.
(d) Ratio of in vitro activity of mpl ligand analog as measured by proliferation assays to amount of mpl ligand analog measured by mpl ligand ELISA.
i- Insertion
NA Not available B. Determination of carbohydrate addition.

The analogs shown in Table 6 were tested to see if they added N-linked carbohydrate using the procedures described in Example 6.

Some analogs (N21, N22, N30, N33, and N36) were also tested with a modified procedure. This was necessary because the monoclonal antibody used to develop the Western blot was raised to a peptide including amino acid residues 47 to 62, and some of the analogs described in Table 6 contain substitutions that affected immunoreactivity with this antibody, e.g. N21. Therefore, to analyze these analogs the supernatants were immunoprecipitated using a monoclonal antibody raised in mice to *E. coli* cell expressed mpl ligand 1-163.

Typically 15 ugs of antibody was used to immunoprecipitate 50 ng of mpl ligand analog. Western blots with immunoprecipitated material were performed as described in Example 6 except the immunoprecipitated bands were visualized by incubating the blots with the rabbit anti-mpl ligand polyclonal antibody (typically 1 ug/ml; raised to *E. coli* cell expressed mpl ligand 1-163) and an anti rabbit ECL kit (Amersham). The results of the various experiments are shown in Table 7. Some of the analogs had increased size indicative of the presence of N-linked carbohydrate (N21, N22, N23, N29, N30, N31, N33, N34, N35, N36, N38, N39, and N40). A subset of these analogs had more than 1 N-linked chain, e.g., N29, N33, N34, N35, N39 and N40. These analogs were secreted at normal or higher levels and had in vitro biological activity comparable to mpl ligand 1-174. This indicates that multiple functional N-linked glycosylation sites can be introduced into mpl ligand without a deleterious effect on either expression or biological activity.

Figure 12:
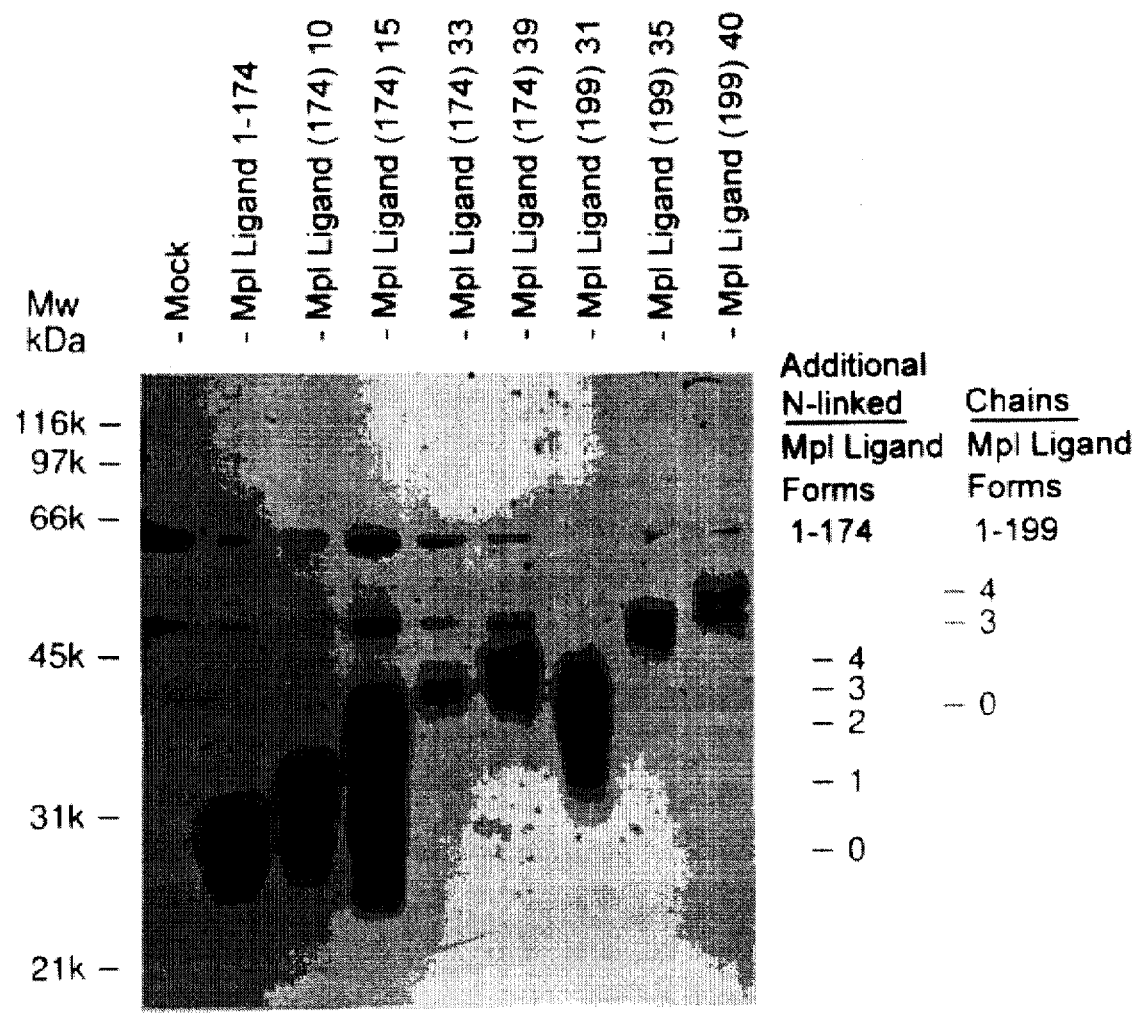
FIG. 12 shows a Western blot analysis of COS-produced mpl ligand 1-174, along with analogs N10, N15, N33, N39, N31, N35, and N40. The number of added N-linked glycosyl sites is also indicated. The figure shows that increasing the number of N-linked sites reduces the mobility of mpl ligand due to increasing amounts of N-linked carbohydrate.

To demonstrate that multiple oligosaccharide chains can be added to mpl ligand, various analogs expressed in COS cells were analyzed by Western blot as described in Example 6. FIG. 12 shows that the mobility of the analogs decreases with increasing numbers of added N-linked glycosylation sites. Analogs with 4 new sites are shown, N39 and N40. The analogs with the most N-linked sites had the slowest mobility. This result is observed with both 1-174 and 1-199 forms of mpl ligand. This indicates that at least 4 analogs can be combined together resulting in new analogs with multiple N-linked carbohydrate chains.

EXAMPLE 16

Comparison of Glycosylation Sites Containing Asn-X-Ser vs. Asn-X-Thr

N-linked glycosylation sites include either Asn-X-Thr or Asn-X-Ser where X can be any one of the 20 naturally occurring amino acids except Pro. We wished to determine whether Ser or Thr is preferred in the third position. Therefore, two sets of analogs with each set containing a mpl ligand glycosylation analog containing either a Ser or Thr at the third position in the sequon were examined to see if there was an effect on percent occupancy of the N-linked glycosylation sites. N15 contains 2 Asn-X-Thr sites while N29 contains 2 Asn-X-Ser sites at exactly the same positions. In a similar manner N30 contains an Asn-X-Ser while N38 contains an Asn-X-Thr at the same position.

Figure 13:
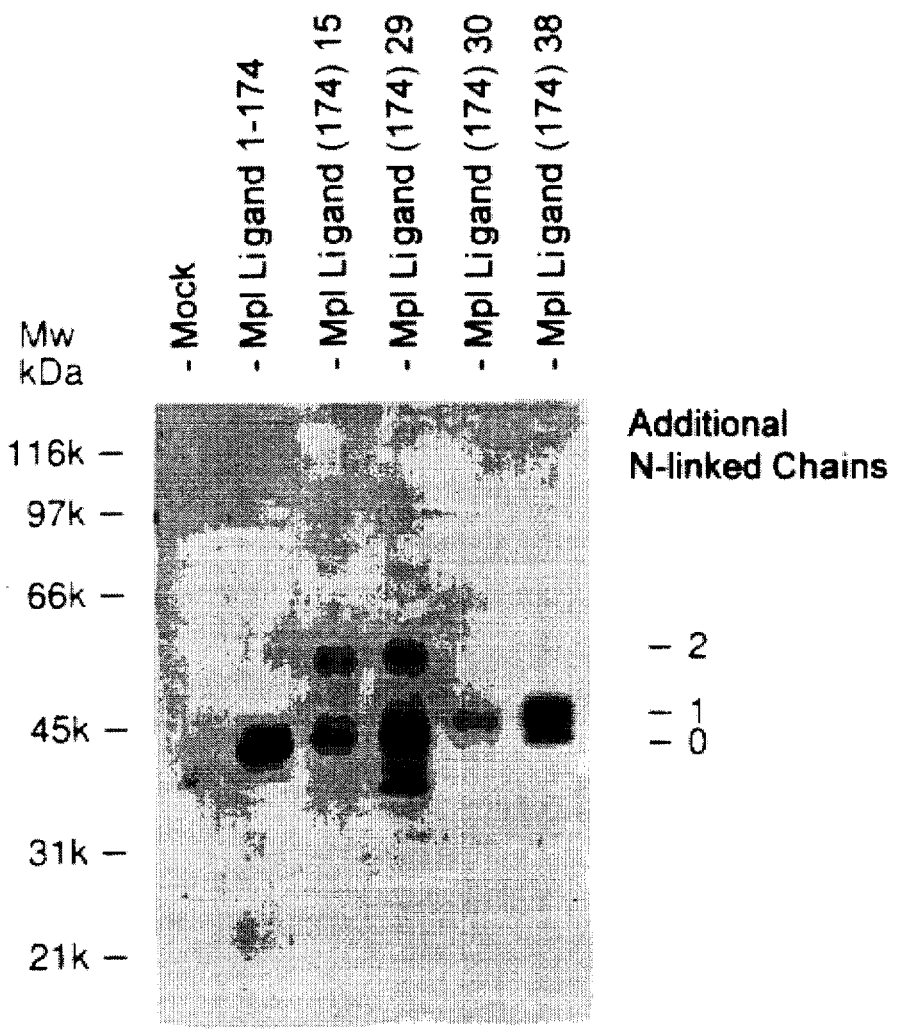
FIG. 13 shows a Western blot analysis of COS-produced mpl ligand 1-174, along with analogs N15, N29, N30, and N38. The number of N-linked glycosyl chains is also indicated.

To compare these two sets of analogs, they were expressed in COS cells and the secreted mpl ligand was subjected to Western analysis as described in Example 6. FIG. 13 shows the results. N15 had a significantly increased proportion of glycosylated mpl ligand as compared to N29. In contrast, there was very little difference in the proportion of glycosylated and unglycosylated mpl ligand when N30 and N38 were compared. These results indicate that both Asn-X-Ser and Asn-X-Thr can be introduced into mpl ligand and that both can act as sites for N-linked carbohydrate addition. In addition, in some cases the Asn-X-Thr sequon may be preferred (i.e., it may be more efficiently glycosylated).

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An analog of mpl ligand, wherein
   (a) said mpl ligand comprises a sequence of amino acids selected from the group consisting of amino acid sequences 7-151 through 1-332, inclusive, of SEQ ID NO: 1,
   (b) said analog of mpl ligand has at least one added N-linked glycosylation site in said sequence of amino acids,
   (c) said analog of mpl ligand has at least one added carbohydrate chain attached to said added N-linked glycosylation site,
   (d) said analog of mpl ligand has a biological activity of specifically stimulating or increasing megakaryocytes or platelets, and
   (e) said analog of mpl ligand is selected from the group consisting of:
   1. [$Asn^{54}$, $Ser^{56}$] mpl ligand;
   2. [$Asn^{52}$, $Thr^{54}$] mpl ligand;
   3. [$Asn^{55(i)}$, $Thr^{57}$] mpl ligand;
   4. [$Asn^{30}$, $Ser^{32}$, $Asn^{120}$, $Ser^{122}$] mpl ligand;
   5. [$Thr^{163}$, $Asn^{164}$] mpl ligand;
   6. [$Asn^{30}$, $Thr^{32}$, $Asn^{120}$, $Thr^{122}$, $Asn^{55(i)}$, $Thr^{57}$] mpl ligand;
   7. [$Asn^{30}$, $Thr^{32}$, $Asn^{55(i)}$, $Thr^{57}$, $Thr^{163}$, $Asn^{164}$] mpl ligand;
   8. [$Asn^{55}$, $Thr^{57}$] mpl ligand;
   9. [$Asn^{56}$] mpl ligand;
   10. [$Thr^{163}$, $Asn^{164}$, $Thr^{166}$] mpl ligand; and
   11. [$Asn^{30}$, $Thr^{32}$, $Asn^{120}$, $Thr^{122}$, $Asn^{55}$, $Thr^{57}$, $Thr^{163}$, $Asn^{164}$, $Thr^{166}$] mpl ligand.

2. An analog of claim 1, wherein the mpl ligand has an amino acid sequence selected from the group consisting of:

| | |
|---|---|
| mpl ligand 1-332 | amino acids 1-332 of SEQ ID NO: 1 |
| mpl ligand 1-199 | amino acids 1-199 of SEQ ID NO: 1 |
| mpl ligand 1-191 | amino acids 1-191 of SEQ ID NO: 1 |
| mpl ligand 1-183 | amino acids 1-183 of SEQ ID NO: 1 |
| mpl ligand 1-174 | amino acids 1-174 of SEQ ID NO: 1 |
| mpl ligand 1-163 | amino acids 1-163 of SEQ ID NO: 1 |
| mpl ligand 1-153 | amino acids 1-153 of SEQ ID NO: 1 |
| mpl ligand 1-152 | amino acids 1-152 of SEQ ID NO: 1 |
| mpl ligand 1-151 | amino acids 1-151 of SEQ ID NO: 1 |
| mpl ligand 7-332 | amino acids 7-332 of SEQ ID NO: 1 |
| mpl ligand 7-191 | amino acids 7-191 of SEQ ID NO: 1 |
| mpl ligand 7-199 | amino acids 7-199 of SEQ ID NO: 1 |
| mpl ligand 7-183 | amino acids 7-183 of SEQ ID NO: 1 |
| mpl ligand 7-174 | amino acids 7-174 of SEQ ID NO: 1 |
| mpl ligand 7-163 | amino acids 7-163 of SEQ ID NO: 1 |
| mpl ligand 7-153 | amino acids 7-153 of SEQ ID NO: 1 |
| mpl ligand 7-152 | amino acids 7-152 of SEQ ID NO: 1, and |
| mpl ligand 7-151 | amino acids 7-151 of SEQ ID NO: 1. |

3. An analog of claim 1, wherein the mpl ligand has an amino acid sequence consisting of amino acids 1-163 of SEQ ID NO: 1.

4. An analog of claim 1, wherein the mpl ligand has an amino acid sequence consisting of amino acids 1-174 of SEQ ID NO: 1.

5. An analog of claim 1, wherein the mpl ligand has an amino acid sequence consisting of amino acids 1-199 of SEQ ID NO: 1.

6. An analog of mpl ligand according to claim 1 which is selected from the group consisting of:
   1. [$Asn^{30}$, $Thr^{32}$, $Asn^{120}$, $Thr^{122}$, $Asn^{55}$, $Thr^{57}$, $Thr^{163}$, $Asn^{164}$, $Thr^{166}$] mpl ligand 1-174; and
   2. [$Asn^{30}$, $Thr^{32}$, $Asn^{120}$, $Thr^{122}$, $Asn^{55}$, $Thr^{57}$, $Thr^{163}$, $Asn^{164}$, $Thr^{166}$] mpl ligand 1-199.

7. An analog according to any of claims 1–6, which is the product of expression of an exogenous DNA sequence in a eukaryotic cell.

8. An analog according to claim 7, wherein said eukaryotic cell is a mammalian cell.

9. An analog according to claim 8, wherein said mammalian cell is CHO.

10. A composition comprising a therapeutically effective amount of an mpl ligand analog according to any of claims 1–6 together with a pharmaceutically acceptable diluent, adjuvant or carrier.

* * * * *

UNITED STATES PATENT AND TRADEMARK OFFICE
CERTIFICATE OF CORRECTION

PATENT NO.   : 5,756,083
DATED        : May 26, 1998
INVENTOR(S)  : Steven G. Elliott It is certified that error appears in the above-identified patent and that said Letters Patent is hereby corrected as shown below:

In Column 21, Table 4, column (d), please delete "units/ml" and insert --units/ng--.

In Column 24, Table 5, second column please delete "IN VITRO" and insert --IN VITRO-- over third column.

Signed and Sealed this

First Day of September, 1998

*Attest:*

BRUCE LEHMAN

*Attesting Officer*     Commissioner of Patents and Trademarks